US008802419B2

(12) United States Patent
Lien et al.

(10) Patent No.: US 8,802,419 B2
(45) Date of Patent: Aug. 12, 2014

(54) MODIFIED PATHOGENS FOR USE AS VACCINES

(75) Inventors: Egil Lien, Cambridge, MA (US); Jon D. Goguen, Holden, MA (US)

(73) Assignee: University of Massachusetts, Boston, MA (US)

( * ) Notice: Subject to any disclaimer, the term of this patent is extended or adjusted under 35 U.S.C. 154(b) by 410 days.

(21) Appl. No.: 12/281,276

(22) PCT Filed: Mar. 2, 2006

(86) PCT No.: PCT/US2006/007443
§ 371 (c)(1),
(2), (4) Date: Mar. 23, 2009

(87) PCT Pub. No.: WO2007/106073
PCT Pub. Date: Sep. 20, 2007

(65) Prior Publication Data
US 2010/0112002 A1  May 6, 2010

(51) Int. Cl.
C12N 1/20 (2006.01)
A01N 63/00 (2006.01)
A61K 48/00 (2006.01)

(52) U.S. Cl.
USPC ............ 435/252.3; 424/93.2; 424/93.4

(58) Field of Classification Search
None
See application file for complete search history.

(56) References Cited

U.S. PATENT DOCUMENTS 6,610,836 B1 * 8/2003 Breton et al. ........... 536/23.1
6,780,414 B2 * 8/2004 Maurelli et al. ........ 424/184.1

FOREIGN PATENT DOCUMENTS

EP  1084709 A1  3/2001

OTHER PUBLICATIONS

Montminy et al (Journal of Leukocyte Biology (Suppl) Sep. 24, 2005, pp. 59-60).*
Bursten et al (Journal of Endotoxin Research vol. 3 (Suppl 1) p. 12, 1996.*
Jones et al (Infection and Immunity vol. 65, No. 11, pp. 4778-4783, 1997).*
Karow et al (Molecular Microbiology vol. 5 (9), pp. 2285-2292, 1991).*
Bainbridge, Brian W., et al. "Expression of a *Porphyromonas gingivalis* lipid A palmitylacyltransferase in *Escherichia coli* yields a chimeric lipid A with altered ability to stimulate interleukin-8 secretion," 8(1):120-129 (Jan. 2006).
Blattner, FR, et al. "The Complete Genome Sequence of *Escherichia coli* K-12" Science, American Association for the Advancement of Science, 277:1453-1462 (Sep. 5, 1997).

Dixon, D R, et al. "Lipopolysaccharide heterogeneity: innate host responses to bacterial modification of lipid a structure," Journal of Dental Research, 84(7): 584-595 (Jul. 2005).
Ellis, C D, et al. "The *Neisseria gonorrhoeae* lpxLII gene encodes for a late-function lauroyl acyl transferase, and a null mutation within the gene has a significant effect on the introduction of acute inflammatory responses," Molecular Microbiology, 42(1): 167-181 (Oct. 2001).
Hallett, A F. "Evaluation of live attenuated plague vaccines in *Praomys* (*Mastomys*) *natalensis*." Infection and Immunity (18)(1):8-13 (Oct. 1977).
Ley, Van Der P., et al.; "Modification of Lipid A Biosynthesis in *Neisseria meningitidis* lpxlmutants: Influence on Lipopolysaccharide structure, Toxicity and Adjuvant Activity," Infection and Immunity, American Society of Microbiology, 69(10):5981-5990 (Oct. 2001).
Montminy, Sara, W., et al. "Virulence factors of *Yersinia pestis* are overcome by a strong lipopolysaccharide response," Nature Immunology; 7(10):1066-1073 (Oct. 2006).
Raetz, C R H, et al. "Lipopolysaccharide Endotoxins," Annual Review of Biochemistry, 71:635-700 (2002).
Rebeil, Roberto, et al. "Variation in lipid A structure in the pathogenic *Yersiniae*," Molecular Microbiology, 52(5):1363-1373 (Jun. 2004).
International Search Report for PCT/US2006/007443 dated Nov. 21, 2007.
Foster et al. (2014) "Adhesion, invasion, and evasion: the many functions of the surface proteins of *Staphylococcus aureus*," Nature Reviews, Microbiology 12: 49-62.
Jong et al. (2012) "Host-pathogen interaction in invasive Salmonellosis," PLOS Pathogens 8(10): 1-9.
Ramachandran (2014) "Gram-positive and gram-negative bacterial toxins in sepsis," Virulence 5:1, 213-218.
Clemenz et al. (1996) "Function of the hTtrB high temperature requirement gene of *Escherichia coli* in the acylation of lipid A: HtrB catalyzed incorporation of laurate," J Biol Chem. May 17, 1996;271(20):12095-102.
Munford et al. (2006 a) "Shield as signal: Lipopolysaccharides and the evolution of immunity to gram-negative bacteria," PLoS Pathog. Jun. 2006;2(6):e67, and.
Munford (2006 b) "Severe sepsis and septic shock: the role of gram-negative bacteremia," Annu Rev Pathol. 1:467-96, Review, and.
Munford et al. (2008) "Sensing gram-negative bacterial lipopolysaccharides: a human disease determinant?" Infect Immun. Feb. 2008;76(2):454-65.

* cited by examiner

*Primary Examiner* — Albert Navarro
(74) *Attorney, Agent, or Firm* — Medlen & Carroll, LLP

(57) ABSTRACT

Described herein are microorganisms that are modified so that they have an increased ability to be recognized by the innate immune system of a eukaryote, relative to an unmodified microorganism. A microorganism may be a gram-negative bacterium that has been modified to produce high potency lipopolysaccharide, e.g., *Yersinia pestis* expressing LpxL. Such modified microorganisms may be used as vaccines for protection against an infection by the unmodified microorganism. They may also be used as delivery vehicles of one or more heterologous antigens, e.g., antigens from pathogens or those associated with a hyperproliferative eukaryotic cell.

20 Claims, 14 Drawing Sheets

FIG 4A-F

Figure 7 A-B
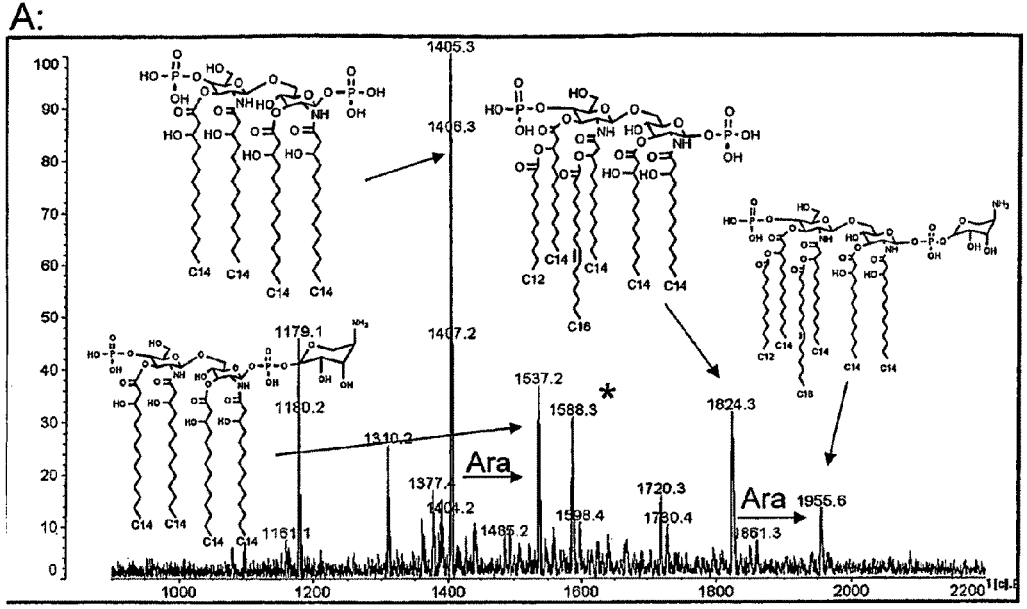
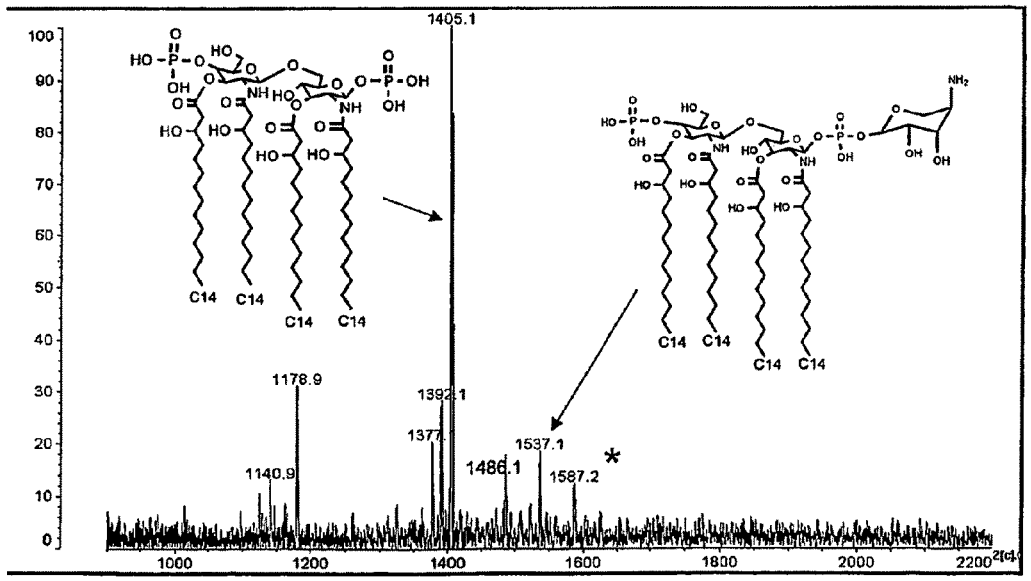

Figure 7 C-D
C:
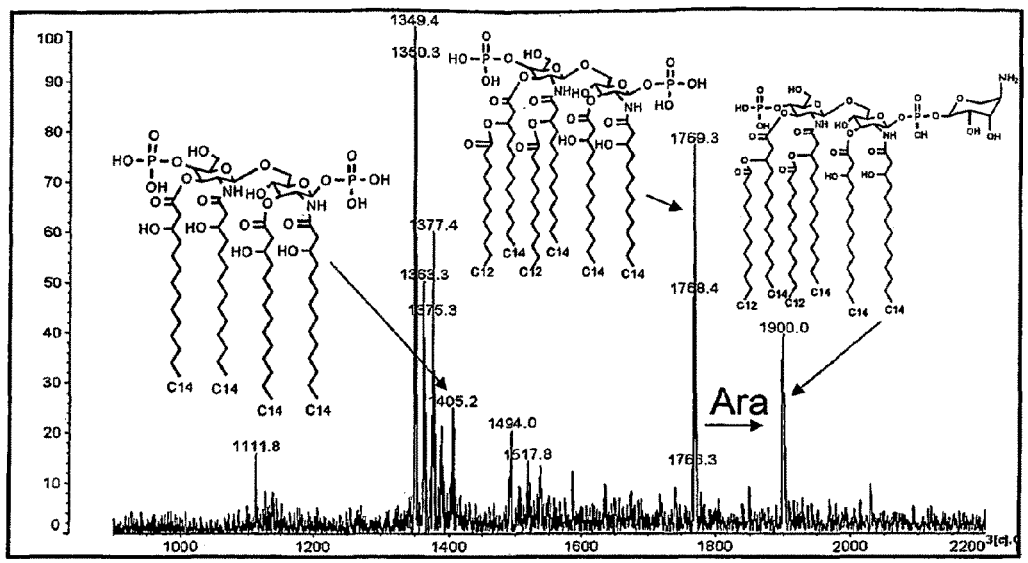
D:
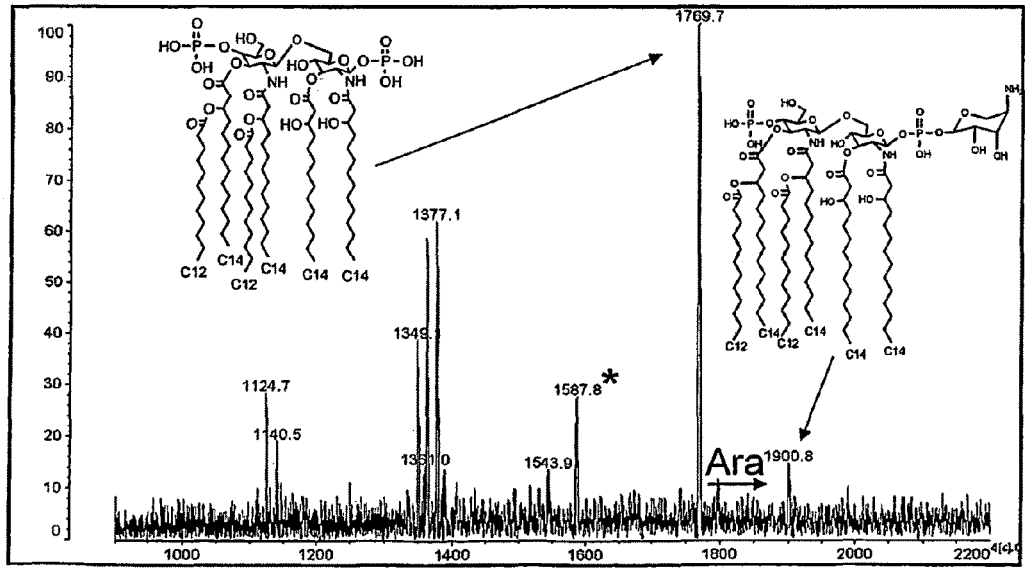

SEQUENCE LISTING

```
<160> NUMBER OF SEQ ID NOS: 4

<210> SEQ ID NO 1
<211> LENGTH: 1468
<212> TYPE: DNA
<213> ORGANISM: Escherichia coli

<400> SEQUENCE: 1
gcgttaatgc cctcatgcgc cagatacact cgcccaaaaa cattcagcgc ggtaaacagc      60
tgatataaag cgtcacgggt cgccttagga tcggcgatgt ggaaatactt gtaaaacgaa     120
atggtggttc gcggttcgct ctcagccaac attttggctt ttagcgcgtc gttggaaatg     180
cggttgtgta acactggcat ggtgtacggt tcctgcgaga tgggaaagta aaaatccgcg     240
gcatgatata gcaattatcg ataattaaca tccacacatt ttacgctaca tttgcgcatt     300
aaaaattatt tgttatttac aagcgcggca atttcgccca gtcttcagcc acaaattttg     360
```

```
gttgcgggcg aaaaaatgcg acaatacata caattgcccg aataggttga aaaacaggat      420
tgatatgacg aatctaccca agttctccac cgcactgctt catccgcgtt attggttaac      480
ctggttgggt attggcgtac tttggttagt cgtgcaattg ccctacccgg ttatctaccg      540
cctcggttgt ggattaggaa aactggcgtt acgttttatg aaacgacgcg caaaaattgt      600
gcatcgcaac ctggaactgt gcttcccgga aatgagcgaa caagaacgcc gtaaaatggt      660
ggtgaagaat ttcgaatccg ttggcatggg cctgatggaa accggcatgg cgtggttctg      720
gccggaccgc cgaatcgccc gctggacgga gtgatcggc atggaacaca ttcgtgacgt      780
gcaggcgcaa aaacgcggca tcctgttagt tggcatccat tttctgacac tggagctggg      840
tgcgcggcag tttggtatgc aggaaccggg tattggcgtt tatcgcccga cgataatcc       900 actgattgac tggctacaaa cctggggccg tttgcgctca aataaatcga tgctcgaccg      960
caaagattta aaggcatga ttaaagccct gaaaaaggc gaagtggtct ggtacgcacc      1020
ggatcatgat tacggcccgc gctcaagcgt tttcgtcccg ttgtttgccg ttgagcaggc     1080
tgcgaccacg accggaacct ggatgctggc acggatgtcc ggcgcatgtc tggtgccctt     1140
cgttccacgc cgtaagccag atggcaaagg gtatcaattg attatgctgc cgccagagtg     1200
ttctccgcca ctggatgatg ccgaaactac cgccgcgtgg atgaacaaag tggtcgaaaa     1260
atgcatcatg atggcaccag agcagtatat gtggttacac cgtcgcttta aaacacgccc     1320
ggaaggcgtt ccttcacgct attaaatctc ccatgccgga tgcttcagaa tggcatccgg     1380
cattaccaca gcaaatcccc ctgatttagc gataaaagct ctctggattg cgcccctgg      1440 aagtcgggcg cataattagt gtgcttat                                       1468

<210> SEQ ID NO 2
<211> LENGTH: 424
<212> TYPE: DNA
<213> ORGANISM: Escherichia coli

<400> SEQUENCE: 2
gcgttaatgc cctcatgcgc cagatacact cgcccaaaaa cattcagcgc ggtaaacagc       60
tgatataaag cgtcacgggt cgccttagga tcggcgatgt ggaaatactt gtaaaacgaa      120
atggtggttc gcggttcgct ctcagccaac attttggctt ttagcgcgtc gttggaaatg      180
cggttgtgta acactggcat ggtgtacggt tcctgcgaga tgggaaagta aaaatccgcg      240
gcatgatata gcaattatcg ataattaaca tccacacatt ttacgctaca tttgcgcatt      300
aaaaattatt tgttatttac aagcgcggca atttcgccca gtcttcagcc acaaattttg      360
gttgcgggcg aaaaaatgcg acaatacata caattgcccg aataggttga aaaacaggat      420
tgat                                                                  424

<210> SEQ ID NO 3
<211> LENGTH: 921
<212> TYPE: DNA
<213> ORGANISM: Escherichia coli

<400> SEQUENCE: 3
atgacgaatc tacccaagtt ctccaccgca ctgcttcatc cgcgttattg gttaacctgg       60
ttgggtattg cgtactttg gttagtcgtg caattgccct acccggttat ctaccgcctc       120
ggttgtggat taggaaaact ggcgttacgt tttatgaaac gacgcgcaaa aattgtgcat      180
cgcaacctgg aactgtgctt cccggaaatg agcgaacaag aacgccgtaa aatggtggtg      240
```

```
aagaatttcg aatccgttgg catgggcctg atggaaaccg gcatggcgtg gttctggccg    300
gaccgccgaa tcgcccgctg gacggaagtg atcggcatgg aacacattcg tgacgtgcag    360
gcgcaaaaac gcggcatcct gttagttggc atccattttc tgacactgga gctgggtgcg    420
cggcagtttg gtatgcagga accgggtatt ggcgtttatc gcccgaacga taatccactg    480
attgactggc tacaaacctg gggccgtttg cgctcaaata aatcgatgct cgaccgcaaa    540
gatttaaaag gcatgattaa agccctgaaa aaaggcgaag tggtctggta cgcaccggat    600
catgattacg gcccgcgctc aagcgttttc gtcccgttgt ttgccgttga gcaggctgcg    660
accacgaccg gaacctggat gctggcacgg atgtccggcg catgtctggt gcccttcgtt    720
ccacgccgta agccagatgg caaagggtat caattgatta tgctgccgcc agagtgttct    780
ccgccactgg atgatgccga aactaccgcc gcgtggatga acaaagtggt cgaaaaatgc    840
atcatgatgg caccagagca gtatatgtgg ttacaccgtc gctttaaaac acgcccggaa    900
ggcgttcctt cacgctatta a                                              921
```

<210> SEQ ID NO 4
<211> LENGTH: 306
<212> TYPE: PRT
<213> ORGANISM: Escherichia coli

<400> SEQUENCE: 4

```
Met Thr Asn Leu Pro Lys Phe Ser Thr Ala Leu Leu His Pro Arg Tyr
1               5                   10                  15

Trp Leu Thr Trp Leu Gly Ile Gly Val Leu Trp Leu Val Val Gln Leu
            20                  25                  30

Pro Tyr Pro Val Ile Tyr Arg Leu Gly Cys Gly Leu Gly Lys Leu Ala
        35                  40                  45

Leu Arg Phe Met Lys Arg Ala Lys Ile Val His Arg Asn Leu Glu
    50                  55                  60

Leu Cys Phe Pro Glu Met Ser Glu Gln Glu Arg Arg Lys Met Val Val
65                  70                  75                  80

Lys Asn Phe Glu Ser Val Gly Met Gly Leu Met Glu Thr Gly Met Ala
                85                  90                  95

Trp Phe Trp Pro Asp Arg Arg Ile Ala Arg Trp Thr Glu Val Ile Gly
            100                 105                 110

Met Glu His Ile Arg Asp Val Gln Ala Gln Lys Arg Gly Ile Leu Leu
        115                 120                 125

Val Gly Ile His Phe Leu Thr Leu Glu Leu Gly Ala Arg Gln Phe Gly
    130                 135                 140

Met Gln Glu Pro Gly Ile Gly Val Tyr Arg Pro Asn Asp Asn Pro Leu
145                 150                 155                 160

Ile Asp Trp Leu Gln Thr Trp Gly Arg Leu Arg Ser Asn Lys Ser Met
                165                 170                 175

Leu Asp Arg Lys Asp Leu Lys Gly Met Ile Lys Ala Leu Lys Lys Gly
            180                 185                 190

Glu Val Val Trp Tyr Ala Pro Asp His Asp Tyr Gly Pro Arg Ser Ser
        195                 200                 205

Val Phe Val Pro Leu Phe Ala Val Glu Gln Ala Thr Thr Thr Gly
    210                 215                 220

Thr Trp Met Leu Ala Arg Met Ser Gly Ala Cys Leu Val Pro Phe Val
225                 230                 235                 240

Pro Arg Arg Lys Pro Asp Gly Lys Gly Tyr Gln Leu Ile Met Leu Pro
                245                 250                 255
```

```
Pro Glu Cys Ser Pro Pro Leu Asp Asp Ala Glu Thr Thr Ala Ala Trp
            260                 265                 270

Met Asn Lys Val Val Glu Lys Cys Ile Met Met Ala Pro Glu Gln Tyr
        275                 280                 285

Met Trp Leu His Arg Arg Phe Lys Thr Arg Pro Glu Gly Val Pro Ser
    290                 295                 300

Arg Tyr
305
```

MODIFIED PATHOGENS FOR USE AS VACCINES

GOVERNMENT SUPPORT

This invention was made with government support under Grant number R01 AI057588 awarded by the National Institutes of Health. The government has certain rights in this invention.

RELATED APPLICATIONS

This application is a 371 national stage application of PCT/US2006/007443, filed Mar. 2, 2006, the entire contents of which are expressly incorporated herein by reference.

BACKGROUND

The spread of anthrax spores via the mail system in the fall of 2001, followed by the death of several American citizens, demonstrated that bioterrorism is a highly relevant threat that can have great impact on people's health and sense of fear. Plague is among the most contagious and lethal bacterial diseases with potential for illegitimate use. Historically, plague has been implicated in large epidemics that were able to change entire societies. Today, smaller plague outbreaks are not uncommon in many countries, and the disease can still induce public panic. The latter is exemplified by the suspected outbreak of pneumonic plague in Surat, India in 1994, leading 600 000 people to flee the town (Perry et al., (1997) Clin Microbiol Rev 10:35).

The causative agent of plague was identified in 1894 as the Gram-negative bacteria *Bacterium pestis*, later called *Yersinia pestis* in honor of Alexandre Yersin (Perry et al., (1997) Clin Microbiol Rev 10:35). Among the species of the genus *Yersinia*, *Y. pestis* is most closely related to *Y. pseudotuberculosis* (Achtman et al., (1999) Proc Natl Acad Sci USA 96:14043). *Y. pestis* is one of history's greatest infectious killers, with the historic plague epidemics claiming as many as 200 million lives by some estimates (Perry et al., (1997) Clin Microbiol Rev 10:35). In the modern US, plague is endemic mainly in the southwestern states, with the most cases occurring in New Mexico. Worldwide, a few thousand cases of plague are reported every year, with a mortality rate usually at 5-10% (WHO (1999) Weekly Epidemiological Record 74:340).

Plague is a zoonotic disease; the bacteria spreads naturally via infected fleas in a rodent reservoir population. The reasons for the cyclic nature of plague epidemics are not defined. However, cycles within rodent populations are believed to play an important role. Once the flea has transferred the bacteria to its host, *Y. pestis* spreads to adjacent lymph nodes, where it rapidly multiplies, causing swollen and necrotic buboes to appear (Butler et al. (1995) In Principles and practice of Infectious Diseases p. 2070) The bacteria can also spread to the blood stream, causing septicemia, and in some cases, secondary pneumonic plague. Pneumonic plague can spread directly from person to person, is highly contagious, and almost 100% lethal when untreated (Ratsitorahina et al. (2000) Lancet 355:111). This is in contrast to bubonic plague, which has a lethality rate of 50-60%. The time from transmission to disease onset varies with the route of infection and the individual, but in general it is assumed an incubation period of 2-6 days for pneumonic plague and 1-7 days for bubonic plague.

Outbreaks of pneumonic plague are rare; the last known case where plague was spread from person to person in the US was 1924-25 (Perry et al., (1997) Clin Microbiol Rev 10:35). However, this might be a clinical course of plague were it to occur during a biological attack (Inglesby et al., (2000) Jama 283:2281). The use of an aerosolized bacteria will cause pneumonic infection. This estimated that 50 kg of *Y. pestis* spread with the wind towards a city of population 5 000 000, will cause 36 000 primary deaths and more than 100 000 deaths in total (WHO (1970) Health Aspects of Chemical and Biological Weapons, Geneva, p. 98). In addition, many people would attempt to flee the city, resulting in further spread of the disease. The establishment of the infection in the rodent population would lead to many subsequent cycles of disease in the area. The mentioned estimate of mortality is based upon treatment of the disease with appropriate antibiotics. Recent studies have reported the emergence of naturally occurring *Y. pestis* resistant to multiple antibiotics in Madagascar (Galimand et al., (1997) N Engl J Med 337:677; Guiyoule et al., (2001) Emerg Infect Dis 7:43). The natural spread of such strains, or the potential use of engineered antibiotic resistant strains in a attack, open the possibility of far more causalities. Therefore, it is of crucial importance to learn more about of the basic biology of *Y. pestis*, and how it interacts with the mammalian immune system. Through increased knowledge, new therapies against the disease can be developed.

*Y. pestis* harbors a very effective type III secretion system, called Ysc. This system allows attachment of the bacteria to the mammalian cell to occur, with the introduction of a channel from the bacterial and host cell cytoplasm. This allows translocation of protein effectors from the bacteria to the host cell cytosol. Many of these effectors act to suppress host cell signaling and phagocytosis (Cornelis et al., (2002) J Cell Biol 158:401; Cornelis et al., (2000) Proc Natl Acad Sci USA 97:8778). Most of the effector are called Yops, and are encoded by the 70 kD plasmid called pCD1 in the two strains for which the genomic sequence is known, KIM and CO92. For example, YopP/YopJ has the ability to strongly affect the signaling via the NF-κB and the MAP kinase pathways, both major inducers of inflammatory signals (Cornelis et al., (2002) J Cell Biol 158:401; Cornelis et al., (2000) Proc Natl Acad Sci USA 97:8778; Cornelis et al., (2000) Proc Natl Acad Sci USA 97:8778). YopH is a powerful phosphotyrosine phosphatase, and can also inhibit phagocytosis. Another potent member of this family is YopE, which has the ability to block signaling molecules via GTPase activating protein, affecting Rac,Rho and CdC42.

In spite of the designation of *Y. pestis* as a NIH/NIAID priority A pathogen, there are currently no licensed US vaccines against plague. A previous formalin-killed whole cell vaccine has been discontinued, and subunit vaccines containing V antigen and F1 capsule protein are still of an exploratory nature (Titball et al., (2004) Opin Biol Ther 4, 965-73). A live EV76-strain vaccine, which is avirulent due to a chromosomal deletion in the pgm locus (delta pgm), is still in use in the former Soviet Union. However, this vaccine may have side effects, and some vaccinated mice have died following inoculation (Titball et al., (2004) Opin Biol Ther 4, 965-73; Russell et al. (1995) Vaccine 13, 1551-6). One common problem with plague vaccines, in particular killed vaccines, has been the failure of these to induce protection against pneumonic plague, the disease form which would be expected following a bioterror attack (Titball et al., (2004) Opin Biol Ther 4, 965-73; Russell et al. (1995) Vaccine 13, 1551-6). Thus, there is a need for better vaccines to protect against both pneumonic and bubonic plague.

SUMMARY

Provided herein are modified microorganisms, e.g., genetically modified microorganisms, for use, e.g., as vaccines. The microorganisms may be modified such that they have an increased ability to be recognized by the innate immune system of a eukaryote, relative to the microorganism that is not modified. For example, a modified microorganism may be one that stimulates a eukaryotic cell receptor involved in innate immune responses, e.g., a Toll-like receptor (TLR). Exemplary modifications include the presence of an immunomodulatory molecule, such as a molecule having adjuvant activity, e.g., particular lipopolysaccharides (LPS or endotoxin). In one embodiment, *Yersinia pestis*, the causative agent of plague, is genetically modified so that it expresses a form of LPS that stimulates the innate immune system of a eukaryote to stronger levels than non modified *Yersinia pestis*.

Exemplary microorganisms provided herein include gram-negative bacteria that make low potency lipopolysaccharide (LPS) comprising one or more heterologous nucleic acids encoding one or more enzymes that permits the bacteria to produce high potency LPS. The high potency LPS preferably activates Toll-like receptor 4 (TLR4) in mammalian cells. The high potency LPS may be hexa-acylated LPS. The heterologous nucleic acid may encode the LPS biosynthetic enzyme LpxL or a functional analog thereof. The gram negative bacterium may be selected from the group consisting of *Yersinia pestis, Chlamydia trachomatis, Francisella tularensis, Legionella pneumophila, Brucella abortus* and *Chlamydia pneumoniae*. In one example, The gram negative bacterium is *Yersinia pestis*, and the heterologous nucleic acid encodes the LPS biosynthetic enzyme LpxL or a functional analog thereof. The enzyme LpxL may be from *E. coli* and may comprise, e.g., SEQ ID NO: 4. A gram negative bacterium as described herein may be alive or killed.

Also provided herein are compositions, e.g., pharmaceutical compositions and vaccines, comprising at least about 100 or 1,000 colony forming units (c.f.u.) of a gram-negative bacterium as described herein. Further provided are methods for making a vaccine for protection against a gram-negative pathogen, comprising combining a modified gram-negative bacterium and a pharmaceutically acceptable carrier.

Other methods provided herein include methods for protecting a mammal from infection by a gram-negative pathogen, comprising, e.g., administering to a mammal in need thereof an effective amount of a vaccine comprising a modified gram-negative bacterium. An exemplary method is a method for vaccination of a mammal against the plague, comprising administering to the mammal a therapeutically effective amount of a modified *Yersinia pestis* bacterium.

Also provided herein are methods for delivering an antigen to a subject, e.g., comprising delivering to a subject in need thereof a therapeutically effective amount of a microorganism modified to express an immunostimulatory molecule, wherein the microorganism further comprises an antigen. The antigen may be from a pathogen, or a cell of the subject against which an immune response is desired.

The modified microorganisms described herein may also be used in methods for identifying an antigen, e.g., in a microorganism. A method may comprise (i) providing a microorganism modified to express an immunostimulatory molecule; (ii) administering the microorganism to an animal; (iii) determining the antigenic specificity of an antibody, B cell and/or T cell of the animal, to thereby identify an antigen in the microorganism. Step (iii) may further comprise obtaining a sample of serum from the animal and determining whether one or more antibodies in the serum are specific for an antigen of the microorganism. A method for determining whether a protein is an antigen may also comprise one or more of the following steps, not necessarily in the order provided: (i) providing a microorganism modified to express an immunostimulatory molecule and further modified to express one or more proteins; (ii) administering the microorganism to an animal; (iii) determining whether one or more antibodies, B cells or T cells of the animal are specific for the one or more proteins. One or more of the proteins may be cancer antigens, antigens associated with an autoimmune disease, and/or antigens from a pathogen.

BRIEF DESCRIPTION OF THE FIGURES

FIG. 1: *Y. pestis* 37° C. LPS contains inhibitory activity. A) Human PBMC were treated with 10 or 100 ng/mL of *Y. pestis* 37° C. LPS or synthetic tetra-acyl lipid $IV_A$, followed by the addition of *Y. pestis* 26° C. LPS or *E. coli* LPS (10 ng/ml) and incubated for 16 hrs. B) HEK 293 cells expressing human TLR4/MD2 were exposed to *Y. pestis* 37° C. LPS (100 and 10 ng/ml), followed by addition of 26° C. *Y. pestis* LPS (10 ng/ml). Cells were incubated for 16 hrs. To study influence on transcription factor activation, HEK293 huTLR4/MD-2 cells were transiently transfected with C) NF-κB- or D) IRF-3 dependent 561 promoter-luciferase reporters, treated with *Y. pestis* 37° C. and/or 26° C. LPS, and incubated for 18 hrs. Lipid concentrations are given in ng/ml.

FIG. 2: Structures of lipid A from *Y. pestis* KIM5 and KIM5 (pMW::lpxL). Lipid A was isolated from bacteria grown in liquid culture at 37° C. or 26° C. The major forms of lipid A were determined by MALDI-TOF mass spectrometry (FIG. 7). Shown are significant lipid A structures found in *Y. pestis* KIM5 at 37° C. A) or 26° C. B), or in KIM5(pMW::lpxL) at both temperatures C). Note that a mixture of different compounds may be present at a given temperature (FIG. 7).

FIG. 3: *Y. pestis* KIM5(pMW::lpxL) synthesizes a potent LPS. HEK293 cells expressing A) human TLR4/MD2 or B) human TLR2 were stimulated with LPS isolated from *Y. pestis* KIM5 grown at 26° C. (♦) or 37° C. (■), *Y. pestis* KIM5(pMW::lpxL) grown at 26° C. (◇) or 37° C. (□), or synthetic lipid $IV_A$ (●) for 18 hrs. Supernatants were analyzed by IL-8 ELISA. Human PBMC isolated from a healthy donor were exposed to LPS as described above for 16 hrs before supernatants were examined for C) TNF or D) IL-6 and IL-8 by ELISA. Peritoneal macrophages were isolated from E) wild type and F) TLR4−/− mice, and stimulated for 16 hrs with different forms of *Y. pestis* LPS and lipid $IV_A$ as described above.

FIG. 4: *Y. pestis* KIM1001(pMW::lpxL) is avirulent in wild type mice. A) Wild type C57Bl/6 mice (n=10 per infection group) were infected subcutaneously (s.c.) with either wild type (wt) *Y. pestis* KIM1001 at 1000 c.f.u. (♦) or 100 c.f.u. (■), or with *Y. pestis KIM*1001(pMW::lpxL) at 1000 cfu (◇) or 100 cfu (□). Survival was monitored every 12 hrs. ($p<0.001$ in comparisons between 1000 c.f.u. LpxL and wt bacteria). B) Wild type mice were infected with increasing doses of KIM1001 and KIM1001(pMW::lpxL). Cumulative results from two* or three** experiments are shown. C) Wild type C57Bl/6 and TLR4−/− mice (n=10 per infection group) were infected s.c. with *Y. pestis* KIM1001 (▲, ■) or KIM1001 (pMW::lpxL) (□, ◇) at a dose of 1000 c.f.u. ($p<0.001$ for KIM1001(pMW::lpxL) vs each of the other groups). D) Colony forming units (c.f.u.) were determined in spleen homogenates from wild type mice infected intravenously (i.v.) or s.c. with KIM1001 or KIM1001(pMW::lpxL). E) TNF concentration in spleen homogenates from i.v. infected mice from D) were measured by ELISA ($p=0.008$ between groups). F) Wild type mice were challenged s.c. with 1000 c.f.u. of KIM1001(pMW::lpxL) or left untreated. Thirty-five days later, mice were infected s.c. with 1000 c.f.u. of KIM1001 and survival was monitored.

FIG. 5. *Y. pestis* grown at 37° C. is a poor stimulator of TLR4 signaling. A) HEK 293 cells stably expressing TLR4/MD-2 or empty vector (pcDNA3) were exposed for 16 hrs to medium alone (white bars) or with heat killed *Y. pestis* KIM5 grown at 37° C. (host temperature, grey bars) or 26° C. (vector temperature, black bars) at a density of $10^7$ bacteria per ml. Supernatants were analyzed for IL-8 contents. B) HEK 293 TLR4/MD-2 cells were transiently transfected with NF-kB- or IRF-3 dependent 561-luciferase reporter constructs and then stimulated with heat killed *Y. pestis* grown at 37° C. or 26° C. Results are given as fold reporter induction above cells exposed to medium alone.

FIG. 6. *Y. pestis* 37° C. LPS inhibits activation of non-human primate cells by 26° C. LPS.
*Y. pestis* KIM 37° C. LPS or synthetic tetra-acylated lipid IVa was added to PBMCs from cynomolgus macaque, followed by addition of KIM5 26° C. LPS. Cells were incubated for 18 hrs and supernatants were analyzed by human IL-8 ELISA. Results indicate that tetra-acylated lipid A/LPS species do not activate non-human primate cells, and can inhibit non-human primate cellular activation by more potent lipid A species in a similar fashion as human cells. Infection of cynomolgus macaque with *Y. pestis* mimics human disease, thus making it a useful non-human primate model system for plague pathogenesis. The LD50 for this primate is approximately 400 c.f.u. by inhalation.

FIG. 7 Mass spectrometry analysis of lipid A from *Y. pestis* KIM5 and KIM5 (pMW::lpxL) grown at 26° C. or 37° C. Wild type *Y. pestis* KIM5 was grown at 26° C. and 37° C. and the lipid A was purified from the whole bacteria by Bligh-Dyer two-phase organic extraction. The lipid was then purified over a DE52 column and analyzed by MALDI-TOF mass spectrometry. The negative ion spectra shown here are representative of multiple extractions. Analysis of the positive ion spectra (not shown) was also done to determine the location of the arabinose at the reducing end of the molecule. Structures are proposed based upon our data compared to previous reports (12,13). (A) At 26° C., the bacteria express at least three different species of lipid A: tetra-acyl lipid A with four C14:0 acyl groups (m/z 1405), a penta-acyl lipid A that has an additional secondary C12:0 acyl chain (m/z 1587), and a hexa-acyl lipid A with additional C12:0 and C16:1 secondary acyl chains (m/z 1824). An additional species (m/z 1179) corresponds to a tri-acyl lipid A that may also be a fragment ion resulting from the loss of an acyl-linked C14:0 group from the tetra-acyl lipid A. In addition, peaks for all four of these species with the addition of an 4-amino-4-deoxy-L-arabinose (L-Ara4N) moiety are also observed (m/z 1310, 1537, 1720 and 1955). (B) When the bacteria is grown at 37° C., they produce predominantly tetra-acyl lipid A. Structural analysis was also carried out for the lipid A from *Y. pestis* KIM5 (pMW::lpxL) expressing the acyltransferase LpxL from *E. coli*. (C) At 26° C. the lipid A revealed the presence of a small amount of tetra-acyl (m/z 1405) and a novel hybrid hexa-acyl species (m/z 1769), which has a C12:0 acyl chain at the 2' secondary position rather than a C16:1 acyl chain. The addition of L-Ara4N was also observed (m/z 1900). The peaks at m/z 1349, 1363 and 1377 (observed more weakly in the other spectra) may not represent tetra-acyl lipid A heterogeneity, since the mature hexa-acyl species appear as single peaks. Hence, they may not be related to lipid A species, and may be other lipids (eg., cardiolipins) recovered from the extraction. (D) At 37° C. the mass spectra were similar, predominantly the hexa-acyl species (m/z 1769) and some penta-acyl lipid A (m/z 1587).

FIG. 8. Non-human primate cells respond to LPS from *Y. pestis* KIM5 (pMW::lpxL) grown at both 26° C. and 37° C. PBMC's isolated from cynomolgus macaque were stimulated with increasing doses of lipid $IV_A$ or LPS isolated from *Y. pestis* KIM5 or KIM5 (pMW::lpxL) grown at 26° C. and 37° C. for 18 hrs, and supernatant was analyzed by human IL-8 ELISA. The cells did not respond to KIM5 37° C. LPS, but strongly to the other forms of LPS, in a similar fashion as the response observed in human PBMC (FIGS. 3*c, d*).

FIG. 9. The presence of pBR322 does not affect KIM1001 virulence. Wild type C57Bl/6 mice (n=5 per group) were infected with 1000 c.f.u. of KIM1001 or KIM1001 (pBR322Δtet) s.c. in the nape of the neck Bacteria were resuspended in 0.05 ml PBS. Survival was monitored every 12 hours.

FIG. 10. *Y. pestis* KIM1001(pMW::lpxL) infection i.v. is associated with increase survival times. Wild type c57Bl/6 or TLR4−/− mice (n=5 per group) were infected with 1000 c.f.u. of KIM 1001 or KIM1001(pMW::lpxL) i.v. in the tail vein. The bacteria were resuspended in a total volume of 0.5 ml PBS. The animals were monitored every 12 hrs for survival.

FIG. 11. LPS biosynthesis pathway in *E. coli* (adapted from Raetz et al. (2002) Ann. Rev. Biochem. 71:635).

DETAILED DESCRIPTION

Modifications

Figure 1:
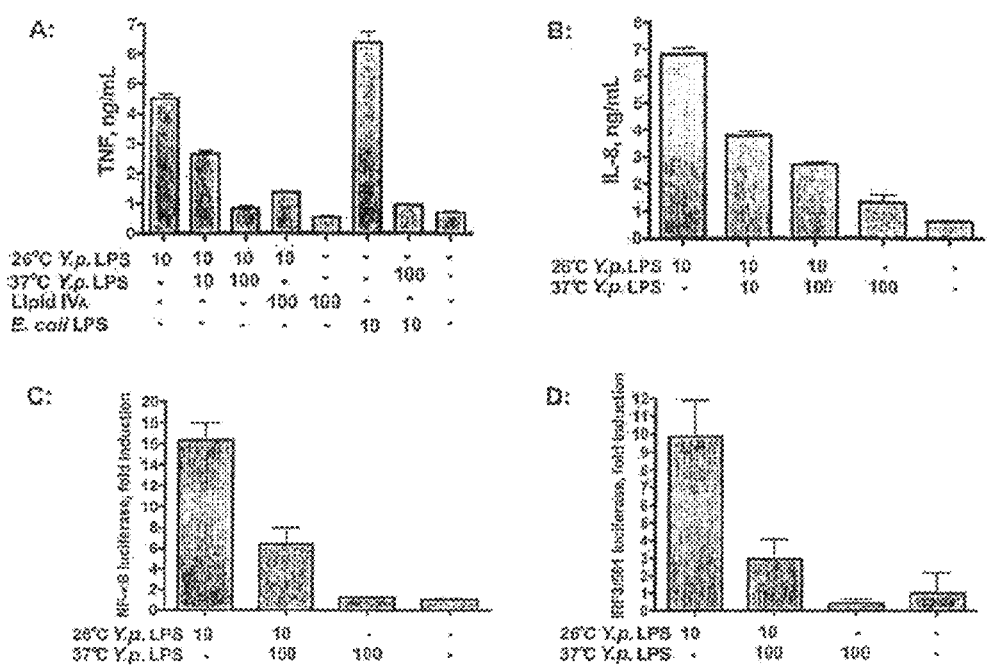

Microorganisms may be modified to contain or express an immunostimulatory molecule or adjuvant, e.g., a molecule that stimulates the immune system and thereby enhances the recognition of the microorganism by the immune system. A preferred immunostimulatory molecule is one that stimulates the innate immune system, generally through "innate" receptors. Innate receptors are receptors that recognize a wide spectrum of conserved pathogenic components. Examples of innate receptors include the toll-like receptors (TLRs) and the intracellular nucleotide-binding site leucine-rich repeat proteins (NODs). Conserved pathogenic components are also referred to as pathogen-associated molecular patterns (PAMPs) and their receptors, which are innate receptors, are referred to as pattern recognition receptors (PRRs).

TLRs are type I transmembrane proteins that are highly conserved from man to plants and *Drosophila*. Most mammalian species have between 10 and 15 types of TLRs. Eleven TLRs have been identified in humans (TLR1-11). TLRs function as dimers and they may also depend on other co-receptors for full ligand sensitivity. For example, TLR-4 associates with MD-2 to recognize LPS, and CD14 and LPS binding protein (LBP) are also involved in this process. TLR-4, which is a lipid A co-receptor exists as four isoforms in humans. The nucleotide and amino acid sequences of isoforms 1-4 are set forth as GenBank Accession numbers NM_138554 and NP_612564 (isoform 1 or A); NM_138556 and NP_612566 (isoform 2 or B); NM_003266 and NP_003257 (isoform 3 or C); and NM_138557 and NP_612567 (isoform 4 or D).

TLR-2 is required for responses to gram-positive bacteria, bacterial lipoproteins, and mycobacteria (Yoshimura et al. (1999) *J Immunol* 163:1; Lien et al. (1999) *J Biol Chem* 274:33419; Takeuchi et al. (1999) *Immunity* 11:443; Means et al. (1999) *J Immunol* 163:3920; Underhill (1999) *Nature* 401:811; Aliprantis et al. (1999) *Science* 285:736; Brightbill et al. (1999) *Science* 285:732; Hirschfeld et al. (1999) *J Immunol* 163:2382.)

In one embodiment, a microorganism is modified to contain a molecule that stimulates an innate receptor, such as a TLR or an NOD in a eukaryote, e.g., a human. The stimulation is preferably sufficiently strong that the administration of a modified microorganism to a eukaryote results in an immune response that is stronger than that resulting from the administration of the unmodified microorganism to the eukaryote. Even more preferably, the stimulation of the innate receptor is such that the administration of the modified microorganism to the eukaryote will result in an immune response or immunoprotective response that will protect the eukaryote from a later infection by the non-modified microorganism. An "immunoprotective response" is an immune response that results in a decrease of symptoms upon infection with a microorganism, e.g., a pathogen, or results in a delay or prevention of a disease associated with infection.

Preferred microorganisms to be modified as described herein are pathogenic microorganisms or infectious agents, such as those that induce an undesirable condition or disease in a eukaryote, e.g., a mammal. A microorganism may be a prokaryotic or a eukaryotic microorganism and may be unicellular or multicellular. Prokaryotic microorganisms include bacteria, such as gram-positive and gram-negative bacteria. Exemplary gram-negative bacteria, include members of the Enterobacteriaceae, Vibrionaceae, Francisellaceae, Legionallales, Pseudomonadacea or Pasteurellaceae groups, including *Salmonella* spp., *Shigella* spp., *Escherichia* spp., *Yersinia* spp., *Vibrio* spp., *Mycobacterium* spp. Pathogenic eukaryotic microorganisms include protozoans and yeast, such as *Candida Albicans, Blastomycosis dermatitides, Blastomycosis brasiliensi, Coccidioides immitis*, and *Cryptococcus neoformans*. A microorganism may also be a virus, e.g., human immunodeficiency virus (HIV)-1. As further discussed below, the type of modification made to the microorganism may depend on the type of microorganism.

A microorganism may be modified by introducing one or more immunostimulatory molecules into the microorganism or by introducing into the microorganism one or more molecules, such as proteins, that are involved in the synthesis of an immunostimulatory molecule. In a preferred embodiment, a microorganism is modified by introducing into the microorganism one or more nucleic acids encoding one or more immunostimulatory molecules or proteins that are involved in the synthesis of one or more immunostimulatory molecules, such that the encoded proteins are expressed in the microorganism. An exemplary nucleic acid is a heterologous nucleic acid, i.e., a nucleic acid that is not normally present in the microorganism, or at least not in that form. It will be understood that it is also possible to modify a microorganism by directly administrating into it one or more immunomodulatory molecules or molecules involved in its synthesis.

Figure 11:
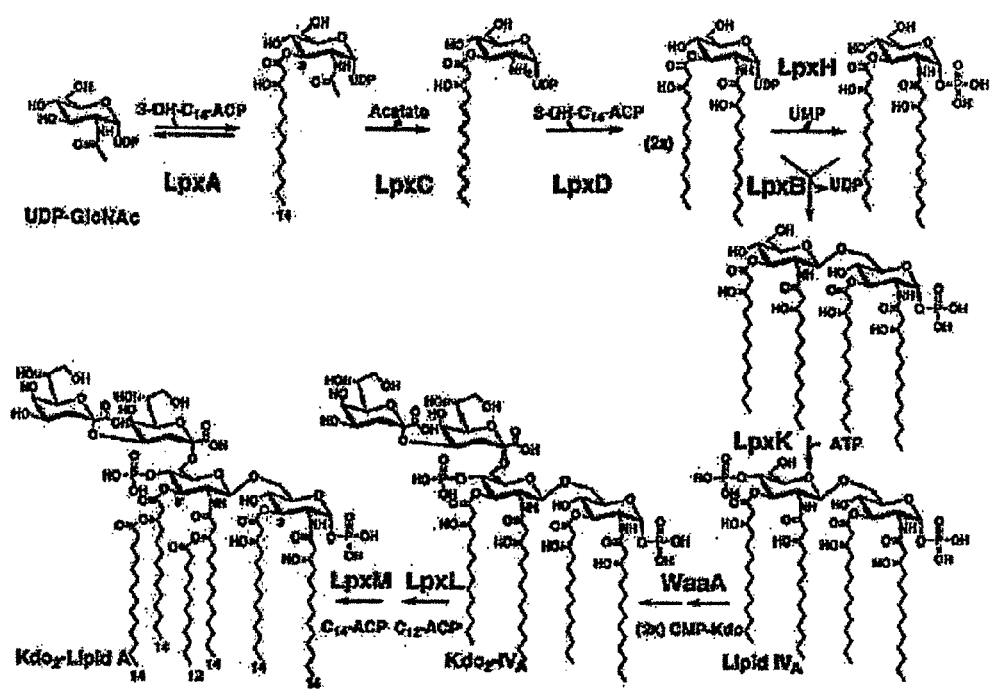

In one embodiment, a microorganism is modified such that it contains or produces an LPS molecule, or lipid A thereof, that stimulates the innate immune system of a eukaryote. Lipopolysaccharide (LPS, endotoxin) is a major part of the outer membrane of gram-negative bacteria (Raetz et al. (2002) *Annu Rev Biochem* 71:635) and is one of the archetypical molecules recognized as foreign by the immune system, a pathogen-associated molecular pattern. LPS is a highly potent activator of the innate immune system, usually with an effect on mononuclear phagocytes at pg/ml concentrations. In many bacteria, LPS consists of lipid A, a di-glucosamine unit covalently modified with fatty acids and phosphate groups; an oligosaccharide core, and a polysaccharide consisting of repeated units of saccharides (also called the O-antigen). Most biological effects of LPS can be mimicked by the lipid A portion, also called the "endotoxic core." The lipid A biosynthetic pathway in *Escherichia coli* is well studied (Raetz et al. (2002) *Annu Rev Biochem* 71:635). A total of nine enzymes are responsible for the assembly of the *E. coli* $KDO_2$-lipid A (FIG. 11).

Figure 2:
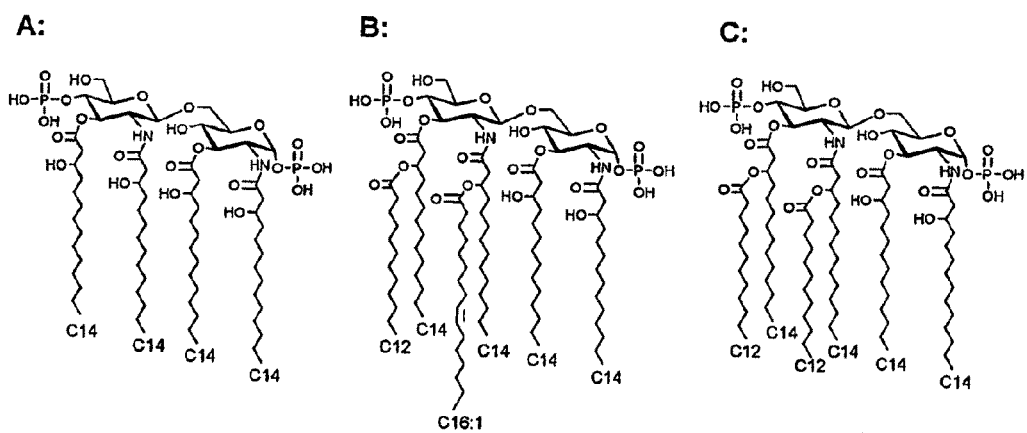
Figure 12:
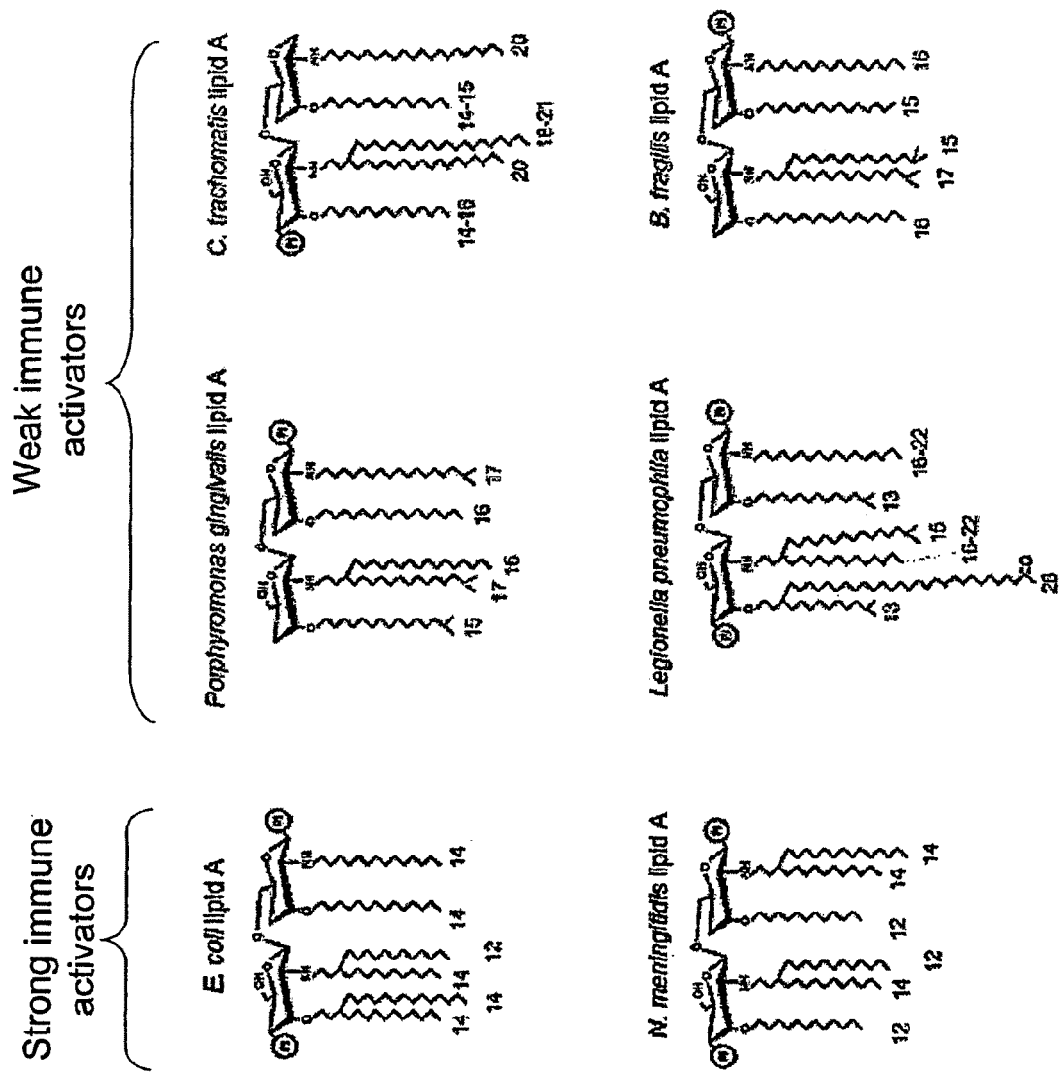
FIG. 12 shows the structures of exemplary high and low potency LPS molecules.
Figure 13:
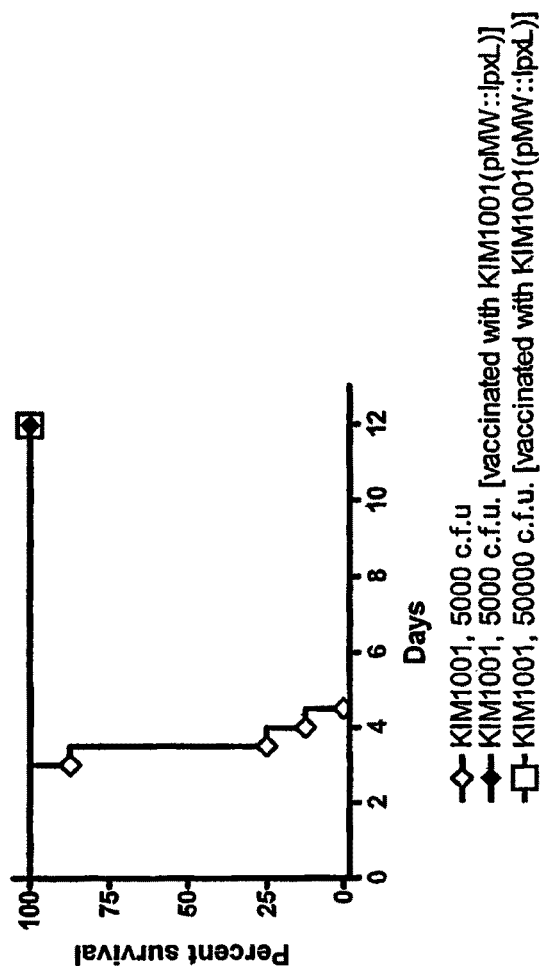
FIG. 13 shows that s.c. vaccination with 100000 c.f.u. of KIM1001 (pMW::lpxL) protects against subsequent intranasal challenge (pneumonic plague model) with 5000 or 50000 c.f.u. of virulent KIM1001.

As further described herein, certain LPS molecules or lipid A portions thereof, are not strong stimulators of the innate immune system. For example, tetra-acylated LPS that is produced by *Yersinia pestis* at 37° C. (see Examples) is essentially inefficient at stimulating the innate immune system. Other LPS molecules, such as hexa-acylated LPS, e.g., shown in FIGS. 2B and 2C, are potent stimulators of the innate immune system. Thus, microorganisms are preferably modified to contain a "high potency LPS" or "strongly stimulatory LPS," i.e., an LPS that stimulates the innate immune system such that a protective immune response is produced, as opposed to a "low potency LPS" or "weakly stimulatory LPS." Typically, there are a few features that may impair lipid A activity: 1) a reduced number of acyl chains (less than six); 2) an increased number of acyl chains (seven); 3) the length of one or more of the acyl chains (short acyl chains, e.g., less than C10, will impair lipid A activity); long acyl chains: longer than, for example, C18); 4) branching of the acyl chains: more branching will impair lipid A activity; and 5) reduced phosphorylation. As an example, monophosphoryl lipid A is much less active and is used as an adjuvant, in natural or synthetic form. Structures of exemplary high potency (strong immune activators) and low potency (weak immune activators) LPS structures are set forth in FIG. 12 (from Erridge et al. (2004) *J. Med. Microbiol.* 53:735).

Thus, for example, a high potency LPS or lipid A molecule may comprise 5 or 6 acyl chains having a length between about C10 and C18 carbons, e.g., between C12 and C16 carbons. These molecules are preferably not significantly phosphorylated and do not have a significant amount of branching.

In one embodiment, a microorganism is modified so that it contains one or more proteins involved in the production of a high potency LPS, such that it produces high potency LPS. For example, a microorganism may be modified by having it express one or more enzymes of the LPS synthetic pathway of a gram-negative bacterium. Exemplary enzymes include the enzymes LpxL, LpxM (also termed HtrB and MsbB, respectively), which are "late" acyl transferases in *E. coli* and several other gram-negative bacteria, and add the final two secondary acyl chains to the tetra-acylated precursor lipid IVa; and LpxP, a third "late" acyl transferase that is also found in *E. coli*. LpxL, LpxM and LpxP from *E. coli* acylates the intermediate (KDO)2-lipid IVA to form (KDO)2-(lauroyl)-lipid IVA. A list of LpxL, LpxM, LpxP and other acyltransferases that are involved in LPS synthesis from various bacteria and the corresponding GenBank Accession numbers is provided in Table 1 below.

TABLE 1

Description of exemplary acyltransferases of gram-negative bacteria

| Enzyme (aliases) | Bacteria | Gene ID | GenBank Acc. nucleotide seq.* | GenBank Acc. amino acid seq. | Conserved regions |
|---|---|---|---|---|---|
| LpxA | Escherichia coli K12 | 944849 | U00096 | NP_414723 | 11-70; 109-179; 3-262 |
| LpxA | Salmonella typhimurium LT2 | 1251746 | AE008705 | NP_459233 | 109-179; 11-70; 3-262 |
| LpxA | Pseudomonas putida KT2440 | 1044942 | AE016779 | NP_743760 | 105-175; 8-68; 1-258 |
| LpxA | Yersinia pestis KIM | 1148070 | AAM83830 | NP_670422 | 114-179; 13-70; 3-262 |
| LpxD | Escherichia coli K12 | 944882 | U00096 | NP_414721 | 104-172; 222-285; 145-245; 1-337; 16-102 |
| LpxD | Salmonella typhimurium LT2 | 1251744 | AE008705 | NP_459231 | 104-172; 222-285; 145-245; 18-337; 18-102 |
| LpxD | Pseudomonas aeruginosa PAOI | 880525 | AE004784 | NP_252336 | 112-183; 203-272; 5-340; 7-105 |
| LpxD | Yersinia pestis KIM | 1148072 | AAM83830 | NP_670424 | 110-180; 222-285; 145-245; 1-337; 4-102 |
| LpxL (htrB, b1054, EG10464, lpxL, waaM) | Escherichia coli K12 | 946216 | U00096 (complement (1114885 . . . 1115805)) | NP_415572; BAA35863; BAA35852; AAC74138 | 4-297 |
| LpxL (htrB) | Escherichia coli CFT073 | 1035020 | AE016759 | NP_753233 | 25-318 |
| LpxL (PSHAa2593) | Pseudoalteromonas haloplanktis TAC125 | 3710222 | CR954246 (2738042 . . . 2738965) | YP_341083; CAI87641 | 6-297 |
| LpxL (BPEN_423) | Candidatus Blochmannia pennsylvanicus str. BPEN | 3562698 | CP000016 (501317 . . . 502256) | YP_277922; AAZ41047 | 4-298 |
| LpxL (HD1106) | Haemophilus ducreyi 35000HP | 1491035 | AE017143 (880973 . . . 881911) | NP_873583; AAP95972 | 8-301 |
| LpxL (CPS_4183) | Colwellia psychrerythraea 34H | 3520374 | CP000083 (4403276 . . . 4404214) | YP_270834; AAZ26125 | 8-301 |
| LpxL (RT0704) | Rickettsia typhi str. Wilmington | 2959130 | AE017197 (complement (898361 . . . 899233)) | YP_067645; AAU04163 | 1-290 |
| LpxL | Salmonella typhimurium LT2 | 1252673 | AE008750 | AAL20805; NP_460126 | 4-297 |
| LpxL | Salmonella enterica subsp. enterica serovar Choleraesuis str. SC-B67 | 3333555 | AE017220 | AAX65803; YP_216089 | 1-270 |
| LpxL | Yersinia pseudotuberculosis IP 32953 | 2955847 | BX936398 | YP_071003 | 4-296 |
| LpxM (msbB, b1855, EG10614, mlt, waaN) | Escherichia coli K12 | 945143 | U00096 (complement (1937246 . . . 1938217)) | NP_416369; AAC74925 | 11-305 |
| LpxM (HD0404) | Haemophilus ducreyi 35000HP | 1490398 | AE017143 (320252 . . . 321208) | NP_872980; AAP95369 | 13-307 |
| LpxM (mxbB) | Salmonella enterica subsp. enterica serovar Typhi Ty2 | 1070298 | AE016837 | NP_804811 | 11-305 |
| LpxM (msbB) | Shigella flexneri | 876657 | AF348706 | NP_085407 | 9-304 |
| LpxM (msbB) | Haemophilus influenzae Rd KW20 | 951108 | U32705 | NP_438368 | 17-309 |
| LpxM (msbB) | Yersinia pestis KIM | 1147194 | AAM85807 | NP_669556 | 12-306 |
| LpxP (ddg, b2378, EG12901, G7241) | Escherichia coli K12 | 946847 | U00096 (2493601 . . . 2494587) | NP_416879; AAC75437 | 26-318 |
| LpxP (ddg, ECA0781) | Erwinia carotovora subsp. atroseptica SCRI1043 | 2884755 | BX950851 (853003 . . . 853935) | YP_048893; CAG73695 | 7-300 |
| LpxP (ddg) | Salmonella typhimurium LT2 | 1253923 | AE008808 | NP_461342 | 6-296 |

TABLE 1-continued

Description of exemplary acyltransferases of gram-negative bacteria

| Enzyme (aliases) | Bacteria | Gene ID | GenBank Acc. nucleotide seq.* | GenBank Acc. amino acid seq. | Conserved regions |
|---|---|---|---|---|---|
| LpxP (ddg) | Shigella flexneri 2a str. 301 | 1023448 | AE005674 | NP_708248 | 26-318 |
| LpxP (ddg) | Yersinia pestis KIM | 1145183 | AAM83830 | NP_667579 | 32-324 |

*The GenBank accession number provides the nucleotide sequence of the genome of the microorganism and the numbers in parentheses represent the location of the sequence encoding the particular protein. These numbers are found in the GenBank entry for the protein.

Whether LpxA, LpxD, LpxL, LpxM and/or LpxP (and/or other enzymes involved in LPS synthesis) are introduced into a microorganism will depend on the microorganism and in particular on whether the microorganism already contains one or more of these or equivalent enzymes. For example, Yersinia pestis may be modified by administration of LpxL only, as it already contains the other enzymes that are necessary for producing high potency LPS. Yersinia pestis strains that may be used include the virulent strain KIM1001 or the avirulent strains KIM5 and EV76, which are avirulent due to the pgm locus deletion. Other species of Yersinia, e.g., Y. pseudotuberculosis, Y. ruckeri, and Y. enterocolitica may also be modified in the same manner as Y. pestis. LpxL may be from E. coli or other bacterium comprising LpxL or a functional analog or homolog thereof, e.g., those in Table 1.

In one embodiment, a Yersinia strain is modified by introducing into it a nucleic acid encoding E. coli LpxL (SEQ ID NO: 4) or a functional analog thereof. For example, a Yersinia strain may be transformed with a nucleic acid comprising, consisting essentially of, or consisting of SEQ ID NO: 1, 2 or 3 or a portion thereof.

Other microorganisms that may be modified to express a high potency LPS are gram-negative bacteria that produce low potency LPS. The following are examples of such gram-negative bacteria: Francisella tularensis, Chlamydia trachomatis, Legionella pneuinophilia, Helicobacter pylori, Bordetella parapertussis, Bordetella pertussis, Brucella abortus, Porphyromonas gingivalis, Bartonella henselae, Coxiella burnetii, Burkholderia cepecia, Bordetella pertussis, Yersinia pseudotuberculosis, Yersinia enterocolitica, Pseudomonas aeruginosa and Chlamydia pneumoniae. Others are provided elsewhere herein.

TABLE 2

Modifications that can be made to other Gram-negative pathogens for use as vaccines

| Organism with putative low TLR4 activation potential | Enzymes from E. coli or other pathogens that can upon expression potentially increase TLR4 reactivity, decrease virulence and hence provide a strategy for the generation of vaccine strains |
|---|---|
| Pseudomonas aeruginosa | LpxA, LpxD, LpxM |
| Porphyromonas gingivalis | LpxA, LpxM, LpxD*, LpxK* |
| Brucella abortus | LpxL, LpxM*, LpxA* |
| Francisella tularensis | LpxA, LpxM, LpxK |
| Burkholderia cepecia | LpxM |
| Bartonella henselae | LpxL, LpxM* |
| Bordetella pertussis | LpxM, LpxA* |

TABLE 2-continued

Modifications that can be made to other Gram-negative pathogens for use as vaccines

| Organism with putative low TLR4 activation potential | Enzymes from E. coli or other pathogens that can upon expression potentially increase TLR4 reactivity, decrease virulence and hence provide a strategy for the generation of vaccine strains |
|---|---|
| Yersinia enterocolitica | LpxL |
| Yersinia pseudotuberculosis | LpxL |
| Chlamydia trachomatis | LpxD, LpxL, LpxM, LpxK* |
| Coxiella burnetii | LpxL, LpxM |
| Bordetella parapertussis | LpxA, LpxM |
| Helicobacter pylori | LpxA, LpxM, LpxL*, LpxD* |
| Bacterioides fragilis | LpxD, LpxL, LpxM, LpxK* |
| Legionella pneumophila | LpxA, LpxD, LpxL, LpxM |
| Prevotella intermedia | LpxM |
| Burkholderia cenocepacia | LpxM |
| Leptospira interrogans | LpxA |

*next to an enzyme indicates that the enzyme may not be absolutely necessary for modifying the particular pathogen.

Other immunostimulatory molecules of the innate immune system include lipopeptides/lipoproteins, lipoarabinomannan, flagelin from bacterial flagella, double-stranded RNA of viruses, the unmethylated CpG islands of bacterial and viral DNA, synthetic/modified versions thereof (including oligonucleotides) and certain other single stranded or double stranded RNA and DNA molecules. Other molecules include bacterial porins (e.g., from Neisseria), lipoteichoic acid, peptidoglycan, synthetic mimics of nucleotides (such as immunostimulants imiquimod and resiquimod/R848 and modified versions thereof). Immunostimulatory molecules, in particular, synthetic ones may be absorbed onto pathogens in order to increase adjuvant effect. In another example, lipoteichoic acid is introduced into the cell walls of gram-positive bacteria. These immunostimulatory molecules are preferably introduced into the cell wall of a microorganism.

Homologs, portions, and homologs of portions of immunomodulatory proteins or proteins producing immunomodulatory molecules, such as the proteins listed in Table 1, may also be used. Portions that can be used include biologically active portions, e.g., proteins comprising, consisting essentially of, or consisting of the conserved or active domains listed in Table 1. Exemplary portions are those comprising, consisting essentially of, or consisting of the catalytically active site of an enzyme, e.g., the site involved in an acyltransferase activity, such as the lipid A acyl transferase domain. Other biologically active portions of proteins may be identified by comparison with related proteins, which comparison may identify other conserved domains that are likely to reflect biologically relevant portions of a protein. Homologs, portions, and homologs of portions of a particular protein that are biologically active are referred to as "functional analogs" or "functional homologs."

Other homologs include those that differ from a wild-type proteins by one or more amino acids, e.g., about 3, 5, 10, 15, 20 or more amino acids. In one embodiment, a microorganism is modified to contain a protein comprising an amino acid sequence that is at least about 80%, 85%, 90%, 95%, 98%, or 99% identical to the amino acid sequence (or portion thereof) of a wild-type or naturally occurring immunostimulatory protein or protein involved in the synthesis of an immunostimulatory protein, such as an enzyme listed in Table 1.

Homologs and analogs can differ from naturally occurring proteins by conservative amino acid differences. For example, conservative amino acid changes may be made, which although they alter the primary sequence of a protein or peptide, do not normally alter its function. Conservative amino acid substitutions typically include substitutions within the following groups: glycine, alanine; valine, isoleucine, leucine; aspartic acid, glutamic acid; asparagine, glutamine; serine, threonine; lysine, arginine (in positions other than proteolytic enzyme recognition sites); phenylalanine, tyrosine.

Any number of procedures may be used for the generation of an analog, such as a mutant, a derivative or a variant of a protein using, e.g., recombinant DNA methodology well known in the art such as, for example, that described in Sambrook et al. (1989, Molecular Cloning: A Laboratory Manual, Cold Spring Harbor Laboratory Press, New York) and Ausubel et al. (1997, Current Protocols in Molecular Biology, Green & Wiley, New York).

A protein may also be modified in a way to form a chimeric molecule comprising the protein of interest fused to another, heterologous polypeptide. A fusion or chimeric protein may comprise a polypeptide of interest fused to a targeting polypeptide or a peptide that allows easy identification or localization of the polypeptide of interest. For example, a protein may be fused to a "Tag sequence encoding a "Tag peptide," such as a hexahistidine tag, myc-epitopes (e.g., see Ellison et al. (1991) J Biol Chem 266:21150-21157) which includes a 10-residue sequence from c-myc, the pFLAG system (International Biotechnologies, Inc.), the pEZZ-protein A system (Pharmacia, N.J.), and a 16 amino acid portion of the *Haemophilus influenza* hemagglutinin protein. Furthermore, any peptide can be used as a Tag peptide so long as a reagent, e.g., an antibody interacting specifically with the Tag peptide, is available or can be prepared or identified. The heterologous polypeptide or peptide preferably does not interfere with the biological function of the polypeptide.

In one embodiment, a microorganism is genetically modified, e.g., modified by introducing into the microorganism one or more nucleic acids that encode one or more immunomodulatory molecules or proteins involved in the production of one or more immunomodulatory molecules. For example, a microorganism may be modified by introducing into it one or more (e.g., 2, 3, 4, or 5) nucleic acids encoding one or more (e.g., 2, 3, 4 or 5) enzymes involved in the production of high potency LPS or lipid A, such as the enzymes listed in Table 1, or one or more functional analogs thereof. In an illustrative embodiment, a nucleic acid comprising, consisting essentially of, or consisting of a nucleotide sequence set forth in Table 1 or a portion thereof encoding a functional analog, is used. A nucleic acid that may be used may comprise, consist essentially of, or consist of a nucleotide sequence that is at least about 80%, 85%, 90%, 95%, 98%, or 99% identical to a nucleotide sequence encoding an immunomodulatory protein or a protein involved in the synthesis of an immunomodulatory molecule, such as those listed in Table 1 or a portion thereof. Other nucleic acids that may used include those that encode a protein that is at least about 80%, 85%, 90%, 95%, 98%, or 99% identical to an immunomodulatory protein or protein involved in the synthesis of an immunomodulatory molecule, such as the enzymes set forth in Table 1, or a portion thereof. Yet other nucleic acids that may be used are those that hybridize, e.g., under high, low, or medium stringency conditions, to a nucleic acid encoding a protein described herein, e.g., a nucleic acid encoding all or a portion of a sequence encoding a protein set forth in Table 1. For example, a microorganism may be modified by introducing into the microorganism one or more nucleic acids that hybridize to one or more nucleic acids consisting of a nucleotide sequence listing in Table 1 or a portion thereof.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul, et al. (1990) *J. Mol. Biol.* 215:403-410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in Altschul et al, (1997) *Nucleic Acids Res.* 25:3389-3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, (1988) *Comput Appl Biosci,* 4:11-7. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

Hybridizations may be conducted under any of the following conditions: high stringency conditions of 0.2 to 1×SSC at 65° C. followed by a wash at 0.2×SSC at 65° C.; low stringency conditions of 6×SSC at room temperature followed by a wash at 2×SSC at room temperature; hybridization conditions including 3×SSC at 40 or 50° C., followed by a wash in 1 or 2×SSC at 20, 30, 40, 50, 60, or 65° C. Hybridizations can be conducted in the presence of formaldehyde, e.g., 10%, 20%, 30% 40% or 50%, which further increases the stringency of hybridization. Theory and practice of nucleic acid hybridization is described, e.g., in S. Agrawal (ed.) Methods in Molecular Biology, volume 20; and Tijssen (1993) Laboratory Techniques in biochemistry and molecular biology-hybridization with nucleic acid probes, e.g., part I chapter 2 "Overview of principles of hybridization and the strategy of nucleic acid probe assays," Elsevier, New York provide a basic guide to nucleic acid hybridization.

Nucleic acids that are introduced into a microorganism may become part of the chromosome of the microorganism or be present extrachromosomally, e.g. on a plasmid. Methods for introducing and expressing nucleic acids, e.g., expression plasmids, in microorganisms are well known. A variety of promoters can be used to express a nucleic acid comprising or consisting of a coding sequence. Similarly a variety of plasmids may be used. Exemplary plasmids include pMW and the mini-Tn7 system.

Exemplary promoters include the promoters that are naturally operably linked to the gene that is being expressed in the microorganism. For example, if *E. coli* LpxL is expressed in a microorganism, e.g., *Yersinia pestis*, the natural *E. coli* promoter of LpxL may be used, e.g., comprising all or a transcriptionally active portion of SEQ ID NO: 1 or 2.

Other promoters for use in *Yersinia* ssp. include promoters from a *Yersinia* virulon gene. A *Yersinia* virulon gene is a gene on the *Yersinia* pYV plasmid, the expression of which is controlled both by temperature and by contact with a target cell. See review by Cornelis et al. (1997). Such genes include genes coding for elements of the secretion machinary (the Ysc genes), genes coding for translocators (YopB, YopD, and LcrV), genes coding for the control elements (YopN and LcrG), and genes coding for effectors (YopE, YopH, YopO/YpkA, YopM and YopP/YopJ).

Vectors may further comprise other sequence elements such as a 3' termination sequence (including a stop codon and a poly A sequence), or a gene conferring a drug resistance which allows the selection of transformants, e.g., *Yersinia* transformants, having received the instant vector.

Nucleic acids, e.g., expression vectors, may be introduced into a pathogen, e.g., *Yersinia*, by a number of known methods. Methods of transformation of microorganisms, e.g., bacteria, include electroporation, calcium phosphate mediated transformation, conjugation, or combinations thereof. For example, a vector can be transformed into a first bacterial strain by a standard electroporation procedure. Subsequently, such a vector can be transferred from the first bacterial strain into a second bacterial strain, e.g., *Yersinia* by conjugation, a process also called "mobilization." *Yersinia* transformants (i.e., *Yersinia* having taken up a nucleic acid) may be selected, e.g., with antibiotics. These techniques are well known in the art. See, for example, Sory et al. (1994).

After modifying a microorganism, it can be tested for determining its ability to stimulate an immune response, e.g., an innate immune response in a eukaryote. A modification that increases the recognition of the microorganism by the immune system of a eukaryote will result in the microorganism having reduced virulence. Virulence may be reduced by at least about 10, $10^2$, $10^3$, $10^4$, $10^5$ or more fold relative to the unmodified microorganism. Tests for virulence depend on the type of microorganism and are known in the art. A modified microorganism may reduce the likelihood of a eukaryote from being affected by the wild-type microorganism by at least 2, 3, 4, 5 or more orders of magnitude. For example, a vaccine may protect at least about 50%, 70%, 80%, 90%, 95%, 99% or 99.9% of individuals immunized. Tests for determining the virulence of a *Yersinia* strain and its immunoprotective effect are set forth in the Examples.

Vaccines

Provided herein are compositions, e.g., pharmaceutical compositions, immunostimulatory compositions and vaccines, comprising modified microorganisms, such as those described herein. Since the modified microorganisms have reduced virulence and preferably are essentially non virulent, they can be used as vaccines to protect a subject from an infection by the unmodified microorganism.

Vaccine or immunogenic compositions may comprise a modified microorganism and a pharmaceutically acceptable carrier. The pharmaceutical carrier or excipient in which the vaccine is suspended or dissolved may be any solvent or solid or encapsulating material such as for a lyophilized form of the vaccine. The carrier is non-toxic to the eukaryote, e.g., vertebrate, and compatible with the microorganism. Suitable pharmaceutical carriers are known in the art and, for example, include liquid carriers, such as normal saline and other non-toxic salts at or near physiological concentrations, and solid carriers, such as talc or sucrose. Gelatin capsules can serve as carriers for lyophilized vaccines. A vaccine may also be presented in the form of an aerosol. Suitable pharmaceutical carriers and adjuvants and the preparation of dosage forms are described in, Remington's Pharmaceutical Sciences, 17th Edition, (Gennaro, Ed., Mack Publishing Co., Easton, Pa., 1985).

The microorganism in a vaccine may be a live microorganism, i.e., the vaccine is a live vaccine. Alternatively, the microorganism in a vaccine is a killed microorganism. Methods for killing microorganisms for vaccine preparations are well know and include, e.g., heat and/or formalin treatment.

A modified microorganism, especially when used as a live vaccine, may further be attenuated, i.e., weakened, e.g., by mutating the microorganism to alter its growth capabilities. In one embodiment, an attenuated vaccine is not replication competent or lacks essential proteins. Methods of making and using live attenuated strains of bacteria that are suitable for vaccines or immunogenic compositions, including instruction on how to make mutations in virulence genes, are taught in U.S. Pat. Nos. 5,294,441, 5,387,744, 5,389,368, 5,468,485, 5,855,879, and 5,855,880.

Methods for attenuating gram-negative bacteria are described, e.g., in U.S. patent publication number 20050136075. For example, *Yersinia* can be attenuated by altering its ysc gene, e.g., by creating a deletion in the gene, such that there is reduced secretion or synthesis of *Yersinia* outer proteins (Yops) (see also U.S. Pat. No. 5,965,381). A Salmonella species, e.g., S. typhi, S. typhimurium, S. minnesota, S. gallinarum and S. pullorum, may be attenuated by altering one or more of the spa, spi, inv, and ssa genes. A Shigella species, e.g., S. dysenteriae, S. boydi, S. flexneri, and S. sonnei, may be attenuated by altering one or more of the spa and mxi genes. An Escherichia species, such as an enterotoxigenic strain (ETEC), an enteropathogenic (EPEC) strain, an enterohemorrhagic (EHEC) strain, a venous thromboses-producing (VTEC) strain, and an enteroinvasive (EIEC) strain, may be attenuated by altering one or more of the ssc, sep and esc genes. A Pseudomonas species, e.g., P. aeruginosa and P. fluorescens, may be attenuated by altering the psc gene. A Bordetella species, e.g., B. avium, B. pertussis, B. bronchiseptica, and B. parapertussis, may be attenuated by altering the bsc gene. A Chlamydia species, e.g., C. psittaci, C. trachomatis, and C. pneumoniae, may be attenuated by altering one or more of the bsc and cds genes. A Vibrio species, e.g., V. cholerae, V. clzolerae O1, V. cholerae non-O1, V. vulnificus, and V. parahaemolyticus, may be attenuated by altering the bsc gene. Attenuation may also be by mutation to the kasugamycin resistance, e.g., by introducing a gene for kasugamycin resistance (Mecsas et al., 2001, Inf 1 mm 67: 2779-2787).

The vaccine, immunogenic composition may also comprise a "balanced-lethal host-vector system," which would enables the microorganism to maintain the presence of the ectopic polynucleotide constructs without the need for external selection (see U.S. application publication No. 20040101531, U.S. Pat. Nos. 5,294,441, 5,387,744, 5,424, 065, 5,656,488, 5,672,345, 5,840,483, 5,855,879, 5,855,880 and 6,024,961, and PCT/US01/13915). The balanced-lethal host-vector system is based upon the concept of having an inactivating mutation in an essential gene of the microorganism, wherein a functional copy of the essential gene is provided on a plasmid (a genetically engineered autonomous extrachromosomal polynucleotide), which contains the polynucleotide that encodes an immunostimulatory protein or protein involved in the synthesis of an immunostimulatory molecule. Thus, in order for the microorganism to remain viable, the plasmid, which contains the functional copy of the essential gene and the polynucleotide that encodes the protein of interest, must be maintained in the carrier bacterium. In one embodiment, the essential gene encodes β-aspartate semialdehyde dehydrogenase (Asd), and the plasmid encodes a functional Asd polypeptide, which complements the chromosomal asd mutation, but which cannot replace the defective chromosomal Asd gene by recombination. Lack of a functional Asd polypeptide causes bacterial cells to lyse. The polynucleotide encoding the functional Asd polypeptide and the polypeptide that encodes the protein of interest are physically linked on the same episome, thereby ensuring that the carrier bacteria maintains the polynucleotide that encodes the protein of interest.

A modified microorganism may also comprise one or more additional heterologous proteins, such as antigens or other immunomodulatory proteins, that will further enhance the immunogenicity of the modified microorganism. For example, a modified microorganism may encode a cytokine or lymphokine that could enhance an immune response. These additional modifications may, e.g., stimulate the adaptive immune response, such as cellular and/or humoral immune responses.

Also provided herein are methods for making a vaccine for immunizing a subject population against infection by a pathogen. The method may comprise providing the pathogen in a modified form as described herein and a pharmaceutically acceptable carrier. Methods for making a modified microorganism may comprise introducing into the microorganism a nucleic acid encoding an immunostimulatory protein or a protein involved in the synthesis of an immunomodulatory molecule.

Also provided are kits, e.g., kits for immunizing a subject against infection by a pathogen. A kit may comprise at least one unit dose of a modified pathogen. A unit dose may be an effective dose to provide immunization against infection by a wild-type strain. Exemplary doses are about $10^2$, $10^3$, $10^4$, $10^5$ or at least about $10^6$ colony forming units (c.f.u.). A vaccine may be provided in a delivery vehicle or container, such as a syringe.

Thus, vaccines based on modified microorganisms as described herein may be used for treating or preventing a condition or disease that is mediated or exacerbated by the corresponding unmodified microorganism. Table 3 set forth below lists various diseases and their causative agents.

TABLE 3

Exemplary microbial diseases and their gram-negative causative agent

| Microorganism | Disease |
|---|---|
| *Yersinia pestis* | bubonic and pneumonic plague |
| *Yersinia enterocolitica* | broad range of gastrointestinal syndromes |
| *Yersinia pseudotuberculosis* | adenitis and septicaemia |
| *Yersinia ruckeri* | enteric redmouth disease (ERM) in salmonids and a few other freshwater fish |
| *Bordetella pertussis* | whooping cough |
| *Bordetella parapertussis* | respiratory disease in humans, e.g., whooping cough and mild pharyngitis, and sheep |
| *Chlamydia pneumoniae* | acute respiratory disease, and contributing to atherosclerosis and heart disease |
| *Chlamydia trachomatis* | conjunctivitis, trachoma (infectious cause of blindness), urethritis, pelvic inflammatory disease (PID) |
| *Pseudomonas aeruginosa* | urinary tract infections, respiratory system infections (in particular in cystic fibrosis patients), dermatitis, soft tissue infections, bacteremia, bone and joint infections, gastrointestinal infections and a variety of systemic infections |
| *Francisella tularensis* | Tularemia, ulceroglandular tularemia, oculoglandular tularemia, pulmonary tularemia, typhoidal tularemia |
| *Legionella pneumophilia* | Legionnaire's disease |
| *Helicobacter pylori* | duodenal ulcers, gastric ulcers, stomach cancer, non-ulcer dypepsia |
| *Brucella abortus* | Brucellosis (Malta fever) |
| *Porphyromonas gingivalis* | periodontal disease |
| *Bartonella henselae* | Cat Scratch Disease and bacillary angiomatosis, bacteremia, and sepsis in immunocompromised patients |
| *Coxiella burnetii* | Q fever |
| *Burkholderia cepecia* | respiratory system infections, in particular in cystic fibrosis patients |

Also provided herein are methods for protecting a subject from a pathogen induced condition or disease, e.g., methods of providing immunity from infection by a wild-type pathogen, e.g., *Yersinia pestis*, to a subject. A method may comprise administering to a subject, e.g., a subject in need thereof, a therapeutically effective amount of a modified form of the microorganism causes a condition or disease (the pathogen), wherein the dose confers immunity on the subject to a disease state caused by the wild-type microorganism. A person in need thereof may be a person that has been exposed to or is likely to be exposed to or infected with a pathogenic microorganism or infectious agent, such as medical personnel or personal that has been exposed to or likely to be exposed to bioterrorism. Other persons at risk of being exposed include, but are not limited to, military personnel, mail handlers, and governmental officials, as well as those with weakened immune systems, for example, the elderly, people on immunosuppressive drugs, subjects with cancer, and subjects infected with HIV.

A vaccine described herein may also be used for reducing the frequency of incidence of a disease that it transmitted by a non-human animal, e.g., plague, in a human population that is contiguous to an animal population reservoir. A method may comprise administering to the animal population a modified microorganism described herein. For example, it may be desirable to immunize rats, which transmit the plague, with a modified *Yersinia pestis* bacterium.

Vaccines or immunogenic compositions may be administered to eukaryotes, such as vertebrates, e.g., mammals, including humans, canines, felines, ovines, bovines, equines, sheep, cattle, livestock and poultry according to several methods.

Methods of administration of a modified microorganism, e.g., in a vaccine preparation, include oral administration, gastric intubation or intranasal administration, e.g., in the form of aerosols, intravenous, intramuscular or subcutaneous injection, vaginal or rectal administration, parenteral administration, for example, intraperitoneal, intraperitoneal, infrasternal, or intra-articular injection or infusion, or by sublingual, oral, topical, or transmucosal administration, by pulmonary inhalation, or through whole body spray (see, e.g., WO 00/04920).

The compositions described herein are preferably given to an individual in a "prophylactically effective amount" or a "therapeutically effective amount," this being sufficient to show benefit to the individual. The actual amount administered, and rate and time-course of administration, will depend, e.g., on the nature and severity of what is being treated or prevented and on the type of microorganism. Prescription of treatment, e.g. decisions on dosage etc, is within the responsibility of general practitioners and other medical doctors.

An effective dose of a vaccine may provide immunity to a virulent pathogen by at least about 2, 3, 4, or 5 or more orders of magnitude more than the level of immunity in a non-immunized subject. An effective dose may comprise, e.g., about $10^3$ to about $10^{12}$ microorganisms per kg body weight of a subject, such as about $10^4$ to about $10^8$ microorganisms per kg body weight of a subject. An effective dose may also comprises about $10^8$ to about $10^{12}$ microorganisms per kg body weight of the subject.

Multiple dosages may be used as needed to provide the desired level of protection. For example, one or more boosters may be needed over time to maintain protection of a eukaryote.

The level of protection provided to a subject after immunization may be determined by methods known in the art, such as by determining the level of antibodies and/or T cells (such as cytotoxic T lymphocytes (CTL)) specific for antigens from the microorganisms, produced in response to the immunization. The presence of specific CTLs can be detected using standard assays such as an assay for $Cr^{51}$ release or for the secretion of IFN-γ. The presence of specific antibodies can be detected by assays such as ELISA using the antigens which are immobilized on a culture plate, or a standard proliferation assay for T-helper cells.

Adjuvants may be added to enhance the antigenicity of a modified microorganism if desired, but are generally not required to induce an effective immune response, since components of the modified microorganisms generally serve as adjuvants. Other agents that may be administered to a subject that is being treated with a vaccine described herein include anti-infectious agents, e.g., anti-fungal compounds, anti-viral compounds, and antibiotics. Antibiotics include, but are not limited to, amoxicillin, clarithromycin, cefuroxime, cephalexin ciprofloxacin, doxycycline, metronidazole, terbinafine, levofloxacin, nitrofurantoin, tetracycline, and azithromycin. Anti-fungal compounds, include, but are not limited to, clotrimazole, butenafine, butoconazole, ciclopirox, clioquinol, clioquinol, clotrimazole, econazole, fluconazole, flucytosine, griseofulvin, haloprogin, itraconazole, ketoconazole, miconazole, naftifine, nystatin, oxiconazole, sulconazole, terbinafine, terconazole, fluconazole, and tolnaftate. Antiviral compounds, include, but are not limited to, zidovudine, didanosine, zalcitabine, stavudine, lamivudine, abacavir, tenofovir, nevirapine, delavirdine, efavirenz, saquinavir, ritonavir, indinavir, nelfmavir, saquinavir, amprenavir, and lopinavir. Anti-infectious agents also include hyper-immune globulin. Hyper-immune globulin is gamma globulin isolated from a donor, or from a pool of donors, that has been immunized with a substance of interest. Specifically, hyper-immune globulin is antibody purified from a donor who was repeatedly vaccinated against a pathogen.

When an agent is administered to a eukaryote that is being administered a modified microorganism, administration of the agent and the modified microorganism may be done simultaneously or sequentially.

Use of Modified Microorganisms as Delivery Vehicles for Heterologous Molecules

The modified microorganisms described herein may also be used as delivery systems, e.g., vaccine delivery systems. This use is based at least in part on the fact that the modified microorganisms have been rendered avirulent and will provide strong adjuvant activity and antigen presentation. In one embodiment, a microorganism modified to express an immunostimulatory molecule is further modified to comprise or express one or more macromolecules, e.g., heterologous macromolecules, against which an immune response is desired. A "heterologous molecule" in a microorganism is a molecule that is not naturally present, e.g., in the same form or amount, in the microorganism. An exemplary macromolecule is a protein, such as a pathogenic antigen. Thus, for example, *Y. pestis* expressing LpxL that also comprises or expresses an antigen from another pathogen, e.g., a bacteria, fungus or virus, may be used to vaccinate a subject and thereby protect the subject from the pathogen. Other proteins that can be delivered to a subject using the modified microorganisms described herein include cancer antigens and antigens associated with autoimmune diseases. The macromolecule, e.g., protein, expressed in the modified microorganism may be one that is known in the art or one that has been identified as further described herein.

Exemplary molecules from pathogens that may be delivered using the vaccine system described herein include antigens from the National Institute of Allergy and Infectious Diseases (NIAID) priority pathogens. These include Category A agents, such as variola major (smallpox), *Bacillus anthracis* (anthrax), *Yersinia pestis* (plague), *Clostridium botulinum* toxin (botulism), *Francisella tularensis* (tularaemia), filoviruses (Ebola hemorrhagic fever, Marburg hemorrhagic fever), arenaviruses (Lassa (Lassa fever), Junin (Argentine hemorrhagic fever) and related viruses); Category B agents, such as *Coxiella burnetti* (Q fever), *Brucella* species (brucellosis), *Burkholderia mallei* (glanders), alphaviruses (Venezuelan encephalomyelitis, eastern & western equine encephalomyelitis), ricin toxin from *Ricinus communis* (castor beans), epsilon toxin of *Clostridium perfringens*;

Staphylococcus enterotoxin B, Salmonella species, Shigella dysenteriae, Escherichia coli strain O157:H7, Vibrio cholerae, Cryptosporidium parvum*; and Category C agents, such as nipah virus, hantaviruses, tickbome hemorrhagic fever viruses, tickbome encephalitis viruses, yellow fever, and multidrug-resistant tuberculosis.

Exemplary antigens that may be delivered include the following ones: *B. anthracis* protective antigen (PA); influenza hemagglutinin (HA), such as from $H5N_1$ influenza; and *Yersinia pestis* LcrV and Cafl. Additional toxins produced by NIAID priority pathogens that are potential targets for this vaccine strategy include ricin, using as antigen a non-toxic ricin mutant selected in yeast (Allen et al. (2005) Yeast 22:1287); a C-terminal heavy chain fragment from botulinum neurotoxin serotype E (Dux et al. (2005) Protein Expr. Purif, in press); and the B subunit of the type II shiga toxin that is the dominant hemorrhagic toxin produced by most enterohemorrhagic strains of *E. coli* (Marcato et al. (2005) Infect. Immun. 73:6523).

Other toxins that may be protected against as described herein, e.g., by including in the modified microorganisms inactivated forms of toxins, such as anatoxin antigens, including toxoids (inactivated but antigenic toxins), and toxoid conjugates include: pertussis toxoid, *Corynebacterium diphtheriae* toxoid, tetanus toxoid, *Haemophilus influenzae* type b-tetanus toxoid conjugate, *Clostridium botulinum* D toxoid, *Clostridium botulinum* E toxoid, toxoid produced from Toxin A of *Clostridium difficile, Vibrio cholerae* toxoid, *Clostridium perfringens* Types C and D toxoid, *Clostridium chauvoei* toxoid, *Clostridium novyi* (Type B) toxoid, *Clostridium septicum* toxoid, recombinant HIV tat IIIB toxoid, *Staphylococcus* toxoid, *Actinobacillus pleuropneumoniae* Apx I toxoid, *Actinobacillus pleuropneumoniae* Apx II toxoid, *Actinobacillus pleuropneumoniae* Apx III toxoid, *Actinobacillus pleuropneumoniae* outer membrane protein (OMP) toxoid, *Pseudomonas aeruginosa* elastase toxoid, snake venom toxoid, *Mannheimia haemolytica* toxoid, *Pasteurella multocida* toxoid, *Salmonella typhimurium* toxoid, *Pasteurella multocida* toxoid, and *Bordetella bronchiseptica* toxoid. Recombinant methods of converting a toxin to a toxoid are known in the art (see, e.g., Fromen-Romano, C., et al., Transformation of a non-enzymatic toxin into a toxoid by genetic engineering, Protein Engineering vol. 10 no. 10 pp. 1213-1220, 1997).

Exemplary viruses from which to protect organisms using modified microorganisms include Coxsackie viruses, cytomegaloviruses, Epstein-Barr viruses, flaviviruses, hepatitis viruses, herpes viruses, influenza viruses, measles viruses, mumps viruses, papilloma viruses, parainfluenza viruses, parvoviruses, rabies viruses, respiratory syncytial viruses, retroviruses, varicella viruses, adenoviruses, arena viruses, bunyaviruses, coronaviruses, hepadnaviruses, myxoviruses, oncogenic viruses, orthomyxoviruses, papovaviruses, paramyxoviruses, parvoviruses, picornaviruses, pox viruses, rabies viruses, reoviruses, rhabdoviruses, rubella viruses, togaviruses, equine herpes virus 1, equine arteritis virus, IBR-IBP virus, and BVD-MB virus. Other viruses include leukemia, lymphotrophic, sarcoma, lentiviruses and other immunodeficiency or tumor viruses. Exemplary lymphotrophic viruses against which a subject may be protected include T-lymphotrophic viruses, such as human T-cell lymphotrophic viruses (HTLVs, such as HTLV-I and HTLV-II), bovine leukemia viruses (BLVS) and feline leukemia viruses (FLVs). Particularly preferred lentiviruses include human (HIV), simian (SIV), feline (FIV) and canine (CIV) immunodeficiency viruses, with HIV-1 and HIV-2 being even more preferred.

Examples of viral antigens to be used include env, gag, rev, tar, tat, nucleocapsid proteins and reverse transcriptase from immunodeficiency viruses (e.g., HIV, FIV); HBV surface antigen and core antigen; HCV antigens; influenza nucleocapsid proteins; parainfluenza nucleocapsid proteins; human papilloma type 16 E6 and E7 proteins; Epstein-Barr virus LMP-1, LMP-2 and EBNA-2; herpes LAA and glycoprotein D; as well as similar proteins from other viruses.

Modified microorganisms comprising an antigen may also be used in methods for conferring a broad based protective immune response against hyperproliferating cells that are characteristic of hyperproliferative diseases, as well as a method of treating individuals suffering from hyperproliferative diseases. As used herein, the term "hyperproliferative diseases" is meant to refer to those diseases and disorders characterized by hyperproliferation of cells. Examples of hyperproliferative diseases include all forms of cancer and psoriasis. In an illustrative embodiment, a method is for treating a subject, such as a subject having or likely to develop a hyperproliferative disease, and comprises administering to the subject a therapeutically effective amount of a modified microorganism expressing an hyperproliferating cell-associated protein or functional homolog thereof. The hyperproliferating cell-associated protein or functional homolog thereof preferably induces an immune response against a cell comprising the hyperproliferating cell-associated protein. As used herein, the term "hyperproliferative-associated protein" is meant to refer to proteins that are associated with a hyperproliferative disease.

In order for the hyperproliferative-associated protein to be an effective immunogenic target, it is preferred that the protein is produced exclusively and/or at higher levels in hyperproliferative cells relative to normal cells. A hyperproliferative-associated protein may be the product of a mutation of a gene that encodes a protein. A mutated gene may encode a protein that is nearly identical to the normal protein except it has a slightly different amino acid sequence, which results in a different epitope not found on the normal protein. Such target proteins include those which are proteins encoded by oncogenes such as myb, myc, fyn, and the translocation genes bcr/abl, ras, src, P53, neu, trk and EGRF. In addition to oncogene products as target antigens, target proteins for anticancer treatments and protective regimens include variable regions of antibodies made by B cell lymphomas, and variable regions of T cell receptors of T cell lymphomas which, in some embodiments, are also used as target antigens for autoimmune diseases. Other tumor-associated proteins can be used as target proteins, such as proteins which are found at higher levels in tumor cells, including the protein recognized by monoclonal antibody 17-1A and folate binding proteins.

Exemplary T cell mediated autoimmune diseases include rheumatoid arthritis (RA), multiple sclerosis (MS), Sjogren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors that bind to endogenous antigens and initiate the inflammatory cascade associated with autoimmune diseases. Vaccination against the variable region of the T cells would elicit an immune response including CTLs to eliminate those T cells.

In RA, several specific variable regions of T cell receptors (TCRs) which are involved in the disease have been characterized. These TCRs include Vβ-3, Vβ-14, Vβ-17 and Vβ-17 (see, e.g., Howell, M. D., et al., 1991 Proc. Natl. Acad. Sci. USA 88:10921-10925; Paliard, X., et al., 1991 Science 253:

325-329; Williams, W. V., et al., 1992 J. Clin. Invest. 90:326-333). Thus, vaccination with a modified microorganism that delivers at least one of these proteins or a functional homolog thereof is expected to elicit an immune response that will target T cells involved in RA.

In MS, several specific variable regions of TCRs which are involved in the disease have been characterized. These TCRs include Vβ-7 and Vα-10 (see, e.g., Wucherpfennig, K. W., et al., 1990 Science 248:1016-1019 and Oksenberg, J. R., et al., 1990 Nature 345:344-346). Thus, vaccination with a modified microorganism that delivers at least one of these proteins or a functional homolog thereof is expected to elicit an immune response that will target T cells involved in MS.

In scleroderma, several specific variable regions of TCRs which are involved in the disease have been characterized. These TCRs include Vβ-6, Vβ3-8, Vβ-14 and Vα-16, Vα-3C, Vα-7, Vα-14, Vα-15, Vα-16, Vα-28 and Vα-12. Thus, vaccination with a modified microorganism that delivers at least one of these proteins or a functional homolog thereof is expected to elicit an immune response that will target T cells involved in scleroderma.

In order to treat patients suffering from a T cell mediated autoimmune disease, particularly those for which the variable region of the TCR has yet to be characterized, a synovial biopsy can be performed. Samples of the T cells present can be taken and the variable region of those TCRs identified using standard techniques. Vaccines can be prepared using this information.

Exemplary B cell mediated autoimmune diseases against which modified microorganisms comprising an antigen may protect a subject include Lupus (SLE), Grave's disease, myasthenia gravis, autoimmune hemolytic anemia, autoimmune thrombocytopenia, asthma, cryoglobulinemia, primary biliary sclerosis and pernicious anemia. Each of these diseases is characterized by antibodies which bind to endogenous antigens and initiate the inflammatory cascade associated with autoimmune diseases. Vaccination against the variable region of such antibodies would elicit an immune response including CTLs to eliminate those B cells that produce the antibody.

In order to treat patients suffering from a B cell mediated autoimmune disease, the variable region of the antibodies involved in the autoimmune activity may have to be identified. If this is the case, a biopsy can be performed and samples of the antibodies present at a site of inflammation can be taken. The variable region of those antibodies can be identified using standard techniques and vaccines can be prepared using this information.

In the case of SLE, one antigen is believed to be DNA. Thus, in patients to be immunized against SLE, their sera can be screened for anti-DNA antibodies and a vaccine can be prepared which includes the variable region of such anti-DNA antibodies found in the sera.

Common structural features among the variable regions of both TCRs and antibodies are well known. The DNA sequence encoding a particular TCR or antibody can generally be found following well known methods such as those described in Kabat, et al. 1987 Sequence of Proteins of Immunological Interest U.S. Department of Health and Human Services, Bethesda Md. In addition, a general method for cloning functional variable regions from antibodies can be found in Chaudhary, V. K., et al., 1990 Proc. Natl. Acad. Sci. USA 87:1066.

Modified microorganisms that are used as delivery vehicles for heterologous antigens may be prepared and administered as further described herein for modified microorganisms.

Methods for Identifying Antigens

Also provided herein are methods for identifying new antigens for use in vaccines. A method may comprise administering to an animal a modified microorganism as described herein and identifying one or more antigens from the microorganism to which the animal raised an immune response, e.g., by determining the antigenic specificity of antibodies in the serum of the animal. The methods may be based at least in part on the following theory. There is a definite linkage between stimulation of innate immunity and the character and quality of the subsequent adaptive immune response. Hence, pathogens which don't stimulate innate immunity very well may produce an adaptive response skewed to a limited repertoire of antigens. A common approach to antigen discovery begins with the analysis of the antigen specificity of B and T cells from individuals who have recovered from infection, on the assumption that these individuals will have adaptive responses to appropriate antigens. If the ability of the pathogen to avoid stimulating innate immunity skews antigenic responses, it may hide valuable antigens from discovery by this approach. Incorporation of adjuvant-like activity into the pathogen, e.g., a bacterium, is expected to enhance the range and strength of specific responses, revealing antigens that might not produce significant response with the wild type pathogen. For example, in *Y. pestis*, the development of subunit vaccines has been limited by the availability of only two antigens that have been clearly shown to be effective: LcrV (V-antigen) and Cafl (F1). The methods described herein, such as comprising administering to an animal an LpxL expressing *Y. pestis*, may be used to identify other antigens of *Y. pestis* that may be used in vaccines, e.g., in subunit vaccines.

An exemplary method for identifying an antigen in a microorganism comprises (i) providing a microorganism modified to express an immunostimulatory molecule; (ii) administering the microorganism to an animal; (iii) determining the antigenic specificity of an antibody, B cell and/or T cell of the animal, to thereby identify an antigen in the microorganism. Determining the antigenic specificity of an antibody, B cell and/or T cell may comprise first obtaining a sample of serum or blood from the animal. Determining the antigenic specificity may also comprise contacting an antibody, B cell or T cell or portion thereof having antigen binding capacity, with one or more macromolecules, e.g., proteins, or portions thereof of the microorganism and determining whether the antibody, B cell or T cell or portion thereof interact with the one or more macromolecules or portions thereof. A method may further comprise formulating the macromolecule or portion thereof in a vaccine formulation for administering to a subject in need of protection against the microorganism comprising the macromolecule.

In an alternative embodiment, a method comprises using a microorganism (the "first microorganism") modified to express an immunostimulatory molecule, wherein the microorganism is further modified to express one or more macromolecules, e.g., proteins, or fragments thereof of another microorganism (the "second microorganism"). For example, for identifying antigens of *Francisella tularensis*, a method may comprise using *Y. pestis* expressing LpxL and further expressing one or more proteins or portions thereof of *Francisella tularensis*. The method may further comprise administering this doubly modified microorganism to an animal and determining whether the animal produced any antibodies or T or B cell that is specific for one or more proteins of *Francisella tularensis*.

In yet another embodiment, a method comprises using a microorganism modified to express an immunostimulatory molecule, wherein the microorganism is further modified to express one or more molecules of a virus, one or more cancer antigens, or any molecule that could be a potential antigen recognized by the immune system of an animal. For example, a method may comprise (i) providing a microorganism that is modified to express an immunostimulatory molecule, wherein the microorganism is further modified to express one or more virus or cancer antigens or portions thereof; (ii) administering the modified microorganism to an animal; and (iii) determining whether the animal raised any antibodies or T or B cell response against one or more of the cancer antigens. Virus or Cancer antigens against which an immune response (e.g., antibodies, T or B cell response) was raised may further be formulated into a vaccine for administration into a subject for treating or preventing the cancer that is associated with the particular cancer antigen. Similarly, antigens of any undesirable cells may be identified by the methods described herein, such as antigens associated with autoimmune diseases, which antigens can then be used in the treatment or prevention of the autoimmune disease.

The microorganisms that may be used in the methods for identifying an antigen include any of the modified microorganisms described herein, such as *Y. pestis* expressing LpxL, or other microorganisms modified following the same principle. Animals to which the microorganisms may be administered include any animal, e.g., a mammal, that is capable of raise an immune response against an antigen, such as rodents, e.g., mice and rats, and rabbits. A microorganism may be administered to the animal in any manner that is likely to result in the animal raising an immune response against the microorganism, e.g., by oral or nasal administration or by parenteral administration, such as intramuscular, subcutaneous or intraperitoneal injection. After a period of time sufficient for the animal to have responded immunologically to the presence of the microorganism, e.g., at least about 7 days, 10 days, 14 days, 21 days or one month, a serum, cell or blood sample may be collected according to methods known in the art. Since the amount and affinity of antibodies (e.g., IgG and IgM) may increase with repeated immunizations, one can also immunize an animal at least 2, 3 or 5 times, prior to obtaining a sample to determine antigenic specificity.

Determining the antigenic specificity of antibodies, e.g., present in the serum or blood of an animal, may be conducted according to methods well known in the art. A method may comprise contacting an antibody or blood or serum or cell sample of an animal with a candidate macromolecule, such as a naturally occurring protein of the microorganism or a portion thereof (e.g., a fragment of at least about 6 amino acids, 10 amino acids, 30 amino acids, 50 amino acids or more) under conditions in which an antibody would bind to an antigen recognized by the antibody. The candidate macromolecule may be labeled, such as with a fluorochrome. A method may further comprise detecting the binding of a candidate macromolecule to the antibody. Similar methods may be used for determining the antigen-binding specificity of a B or T cell. Furthermore, reactive cell subsets may be used in proliferation assays following exposure to the specific antigen.

Antigens identified as described herein may be prepared in vaccine formulations. For example, one or more antigens or portion thereof, may be combined with a pharmaceutically acceptable carrier. Alternatively, one or more nucleic acids encoding one or more antigens or portion thereof may be formulated into a therapeutic composition and administered to a subject in need thereof. A nucleic acid may comprise a promoter that is operably linked to the sequence that encodes an antigen or portion thereof. A nucleic acid may be in the form of a vector, e.g., an expression vector.

It is possible to express at least about 2, 3, 5, 10, or 25 proteins in a microorganism, thereby increasing the likelihood of identifying one or more of these proteins as antigens that can be used in vaccines. As another way to adapt this method to a high throughput method, libraries of macromolecules may be tested or screened for binding of antibodies, B cells or T cells of the animal to whom a modified microorganism was administered.

The present description is further illustrated by the following examples, which should not be construed as limiting in any way. The contents of all cited references (including literature references, issued patents, published patent applications and GenBank Accession numbers as cited throughout this application) are hereby expressly incorporated by reference. When definitions of terms in documents that are incorporated by reference herein conflict with those used herein, the definitions used herein govern.

EXAMPLES

Example 1

Evasion of Endotoxin Signaling is Critical for the Virulence of *Yersinia pestis* Summary The Gram-negative bacterium *Yersinia pestis*, causative agent of plague, efficiently escapes containment by the innate immune system. Toll-like receptor-4 (TLR4) is central in innate recognition of gram-negative endotoxin/lipopolysaccharide (LPS). *Y. pestis* LPS is highly inflammatory in bacteria grown at temperatures prevailing in its flea vector, but weakly stimulatory during growth at 37° C. Here we describe how the resulting evasion of TLR4-signaling is required for *Y. pestis* virulence. When modified to produce potent LPS at 37° C., normally lethal *Y. pestis* is rendered avirulent for wild type mice, but remains virulent in TLR4−/− animals. The modified strain also acts as a vaccine against virulent *Y. pestis*.
One-Sentence Summary The Gram-negative pathogen *Yersinia pestis*, the causative agent of plague, modifies its lipopolysaccharide at host temperature (37° C.), and we find that this modification is necessary for its virulence by evasion of Toll-like receptor 4 signaling.
Body Text:

The Gram-negative bacterium *Yersinia pestis*, causative agent of plague, produces a fulminant systemic infection following inoculation of a few bacteria into the skin by flea bite (1). The key to the extreme virulence of *Y. pestis* is escape from innate antibacterial defenses (1, 2). The activation of Toll-like receptor 4 (TLR4) by endotoxin (lipopolysaccharide, LPS), a major component of the Gram-negative outer membrane, is a major pathway inducing host innate immune responses to native bacteria (3-7). The immune-activating moiety of LPS is lipid A, a di-glucosamine unit with covalently attached acyl chains, which interacts with TLR4 and MD-2 to induce cellular responses (3-8). Lipid A structure is conserved among Gram-negatives but is not invariant. The number and structure of acyl chains varies among species, is influenced by environment, and is often heterogeneous even within a single species (6, 9, 10). It has been hypothesized that production of weakly stimulatory LPS plays a role in virulence of several Gram-negative pathogens (10). Hexa-acylated structures are found in *Y. pestis* grown at 21° C. to 27° C. (ambient/flea temperatures), but LPS is predominantly tetra-acylated at 37° C. (host temperature)

(11-13). Hexa-acylated LPS/lipid A is normally a strong activator of human cells, whereas tetra-acylated lipids have lower stimulatory activity (4, 11, 12, 14, 15). It has been suggested that the temperature-dependent remodeling of lipid A structure could be necessary for *Y. pestis* to achieve the high bacterial load in mammalian blood required for efficient flea infection prior to the induction of lethal shock. *Y. pestis* may also need to minimize TLR4 stimulation early in infection to prevent containment by local inflammation.

Figure 5:
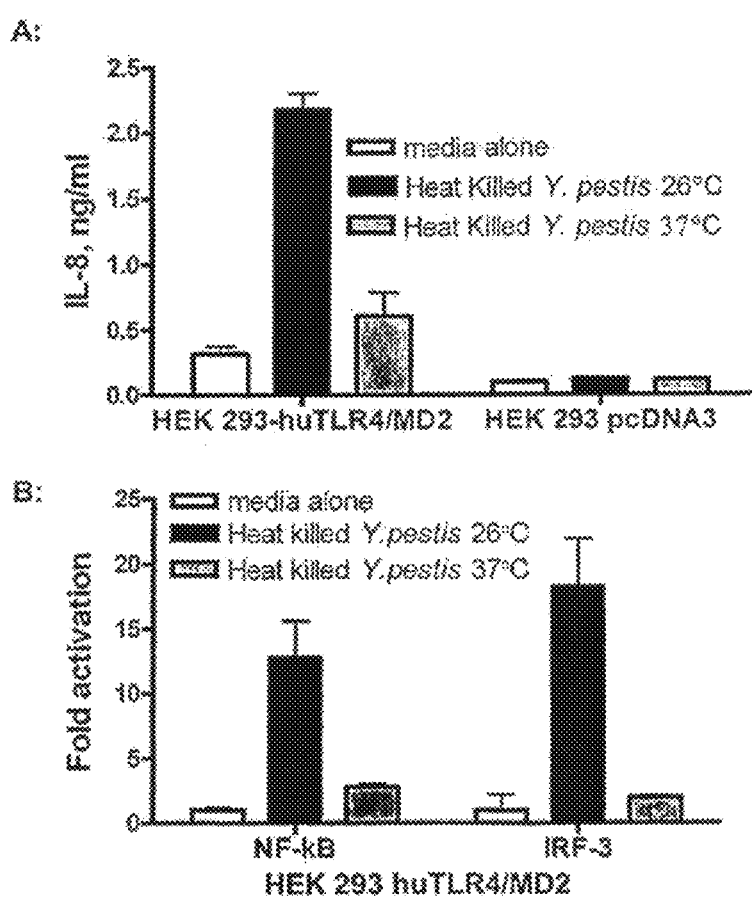
Figure 6:
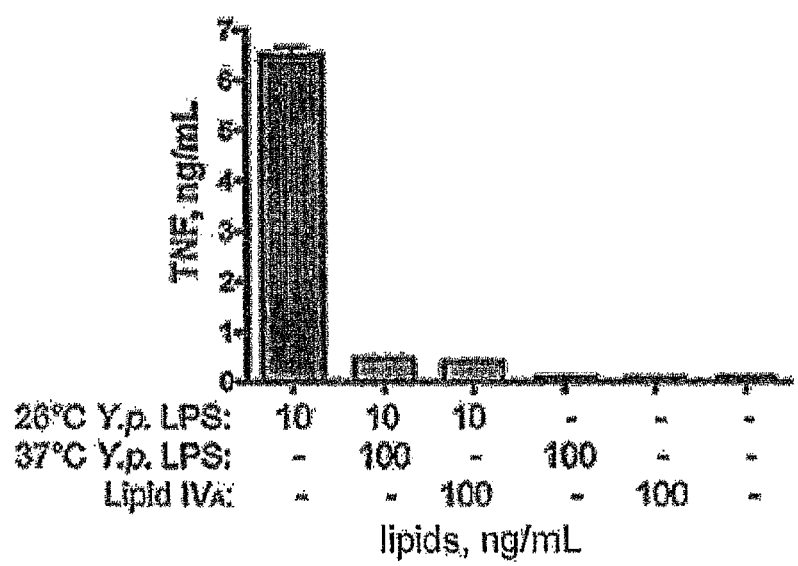

*Y. pestis* grown at 37° C. poorly activated TLR4 signaling (FIG. 5). Since tetra-acylated LPS may antagonize activity induced by potent endotoxin (4, 14, 15), we also analyzed the anti-inflammatory role of 37° C. *Y. pestis* LPS. LPS purified from *Y. pestis* KIM5 grown at 26° C., but not 37° C. (16), activated human peripheral blood mononuclear cells (PBMC) (FIG. 1A) and HEK293 huTLR4/MD-2 cells (FIG. 1B). Activation induced by 26° C. *Y. pestis* LPS and *Escherichia coli* LPS was inhibited by 37° C. *Y. pestis* LPS and by the synthetic tetra-acylated lipid IV$_A$ in human PBMC (FIG. 1A). Stimulation of HEK293 huTLR4/MD-2 cells assayed by interleukin (IL)-8 release (FIG. 1B) and activation of NF-κB and IRF-3 dependent reporters (FIGS. 1C,D) by the 26° C. LPS was also inhibited by the 37° C. preparation. We also observed repression of cytokine release in PBMC from cynomolgus macaque (*Macaca fascicularis*) (FIG. 6), a model organism for studies of plague in primates. Bacteria may well contain a mixture of stimulatory and non-stimulatory LPS species, especially during transition between flea and host temperatures, with the antagonistic activity of tetra-acylated LPS blunting induction of innate immunity by the active LPS species.

Mass spectroscopy analysis showed mainly tetra-acylated *Y. pestis* lipid A in *Y. pestis* KIM5 grown at 37° C., with hexa-acylated structures present only at the lower temperature (FIGS. 2A,B, FIGS. 7A,B). LpxL (HtrB) and LpxM (MsbB) are "late" acyltransferases in *E. coli* and several other Gram-negative bacteria, adding the secondary acyl chains to the tetra-acylated precursor lipid IV$_A$ (6). LpxP, a third late *E. coli* acyltransferase, is active at low temperatures (6, 17, 18). We could identify only two late acyltransferases, lpxP and lpxM, in the *Y. pestis* genome (19-21). This suggests that the lack of LpxL together with the temperature sensitivity of LpxP is responsible for the absence of hexa-acylated lipid A at 37° C.

We cloned lpxL from *E. coli* K12, and expressed the gene in *Y. pestis* KIM5 under control of its own promoter on the vector pBR322 [*Y. pestis* KIM5(pMW::lpxL)](16). The nucleotide sequence of the promoter and the sequence encoding LpxL is set forth below (the promoter sequence and 3' untranslated region are set forth in lower case and the sequence encoding LpxL is set forth in upper case):

```
                                        (SEQ ID NO: 1)
gcgttaatgccctcatgcgccagatacactcgcccaaaaacattcagcgc ggtaaacagctgatataaagcgtcacgggtcgccttaggatcggcgatgt ggaaatacttgtaaaacgaaatggtggttcgcggttcgctctcagccaac attttggcttttagcgcgtcgttggaaatgcggttgtgtaacactggcat ggtgtacggttcctgcgagatgggaaagtaaaaatccgcggcatgatata gcaattatcgataattaacatccacacattttacgctacatttgcgcatt aaaaattatttgttatttacaagcgcggcaatttcgcccagttcttcagc cacaaattttggttgcgggcgaaaaaatgcgacaatacatacaattgccc
``` gaataggttgaaaaacaggattgatATGACGAATCTACCCAAGTTCTCCA

CCGCACTGCTTCATCCGCGTTATTGGTTAACCTGGTTGGGTATTGGCGTA

CTTTGGTTAGTCGTGCAATTGCCCTACCCGGTTATCTACCGCCTCGGTTG

TGGATTAGGAAAACTGGCGTTACGTTTTATGAAACGACGCGCAAAAATTG

TGCATCGCAACCTGGAACTGTGCTTCCCGGAAATGAGCGAACAAGAACGC

CGTAAAATGGTGGTGAAGAATTTCGAATCCGTTGGCATGGGCCTGATGGA

AACCGGCATGGCGTGGTTCTGGCCGGACCGCCGAATCGCCCGCTGGACGG

AAGTGATCGGCATGGAACACATTCGTGACGTGCAGGCGCAAAAACGCGGC

ATCCTGTTAGTTGGCATCCATTTTCTGACACTGGAGCTGGGTGCGCGGCA

GTTTGGTATGCAGGAACCGGGTATTGGCGTTTATCGCCCGAACGATAATC

CACTGATTGACTGGCTACAAACCTGGGGCCGTTTGCGCTCAAATAAATCG

ATGCTCGACCGCAAAGATTTAAAAGGCATGATTAAAGCCCTGAAAAAAGG

CGAAGTGGTCTGGTACGCACCGGATCATGATTACGGCCCGCGCTCAAGCG

TTTTCGTCCCGTTGTTTGCCGTTGAGCAGGCTGCGACCACGACCGGAACC

TGGATGCTGGCCACGGATGTCCGGCGCATGTCTGGTGCCCTTCGTTCCACG

CCGTAAGCCAGATGGCAAAGGGTATCAATTGATTATGCTGCCGCCAGAGT

GTTCTCCGCCACTGGATGATGCCGAAACTACCGCCGCGTGGATGAACAAA

GTGGTCGAAAAATGCATCATGATGGCACCAGAGCAGTATATGTGGTTACA

CCGTCGCTTTAAAACACGCCCGGAAGGCGTTCCTTCACGCTATTAAatct cccatgccggatgcttcagaatggcatccggcattaccacagcaaatccc cctgatttagcgataaaagctctctggattgcgcccctggaagtcgggc gcataattagtgtgcttat.

The promoter sequence (sequence in lower case located 5' to the sequence encoding LpxL) is provided as SEQ ID NO: 2 and the nucleotide sequence encoding the LpxL protein is provided as SEQ ID NO: 3.

The amino acid sequence of LpxL encoded by SEQ ID NOs: 1 and 3 is set forth below:

```
                                        (SEQ ID NO: 4)
MTNLPKFSTALLHPRYWLTWLGIGVLWLVVQLPYPVIYRLGCGLGKLALR

FMKRRAKIVHRNLELCFPEMSEQERRKMVVKNFESVGMGLMETGMAWFWP

DRRIARWTEVIGMEHIRDVQAQKRGILLVGIHFLTLELGARQFGMQEPGI

GVYRPNDNPLIDWLQTWGRLRSNKSMLDRKDLKGMIKALKKGEVVWYAPD

HDYGPRSSVFVPLFAVEQAATTTGTWMLARMSGACLVPFVPRRKPDGKGY

QLIMLPPECSPPLDDAETTAAWMNKVVEKCIMMAPEQYMWLHRRFKTRPE

GVPSRY.
```

Figure 3:
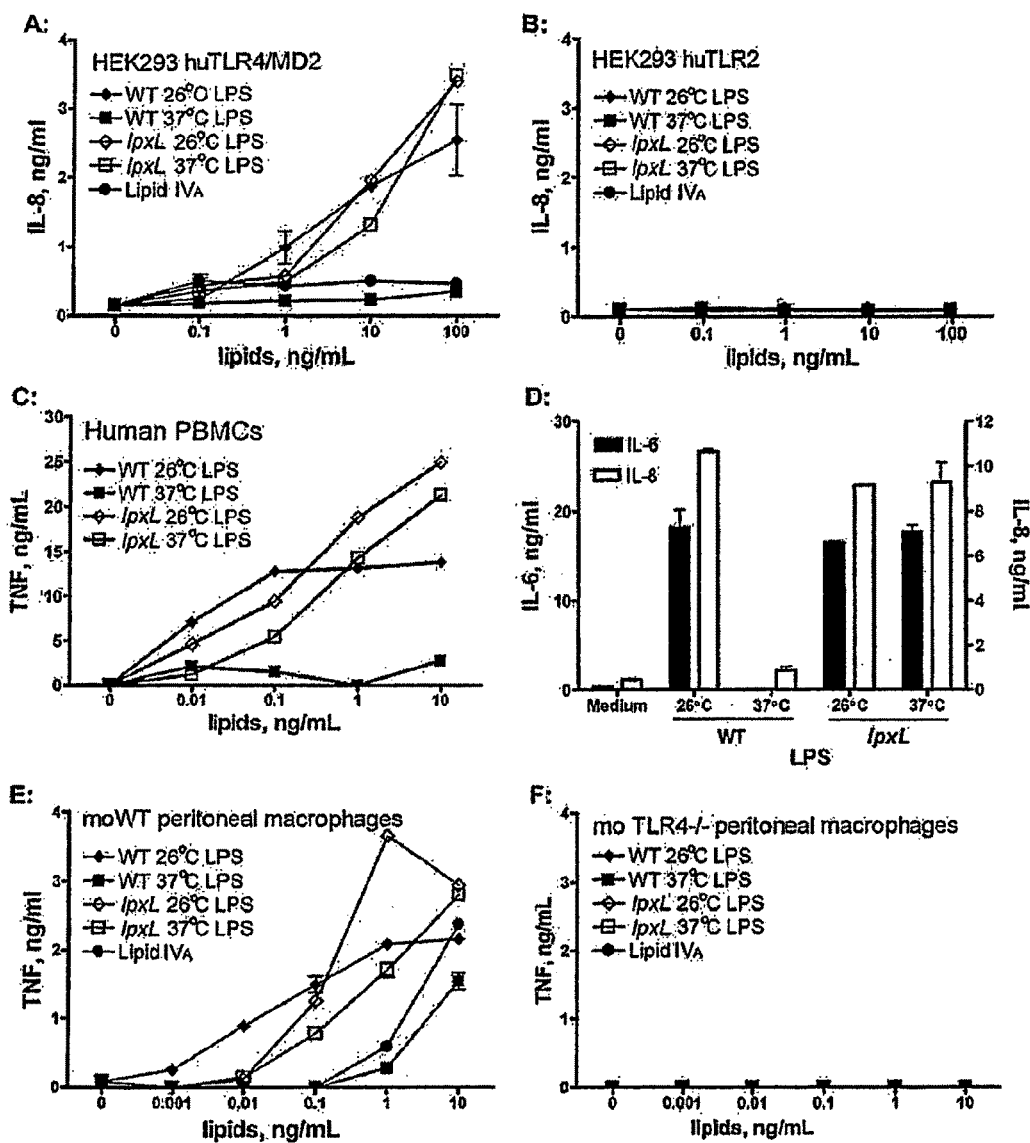
Figure 4:
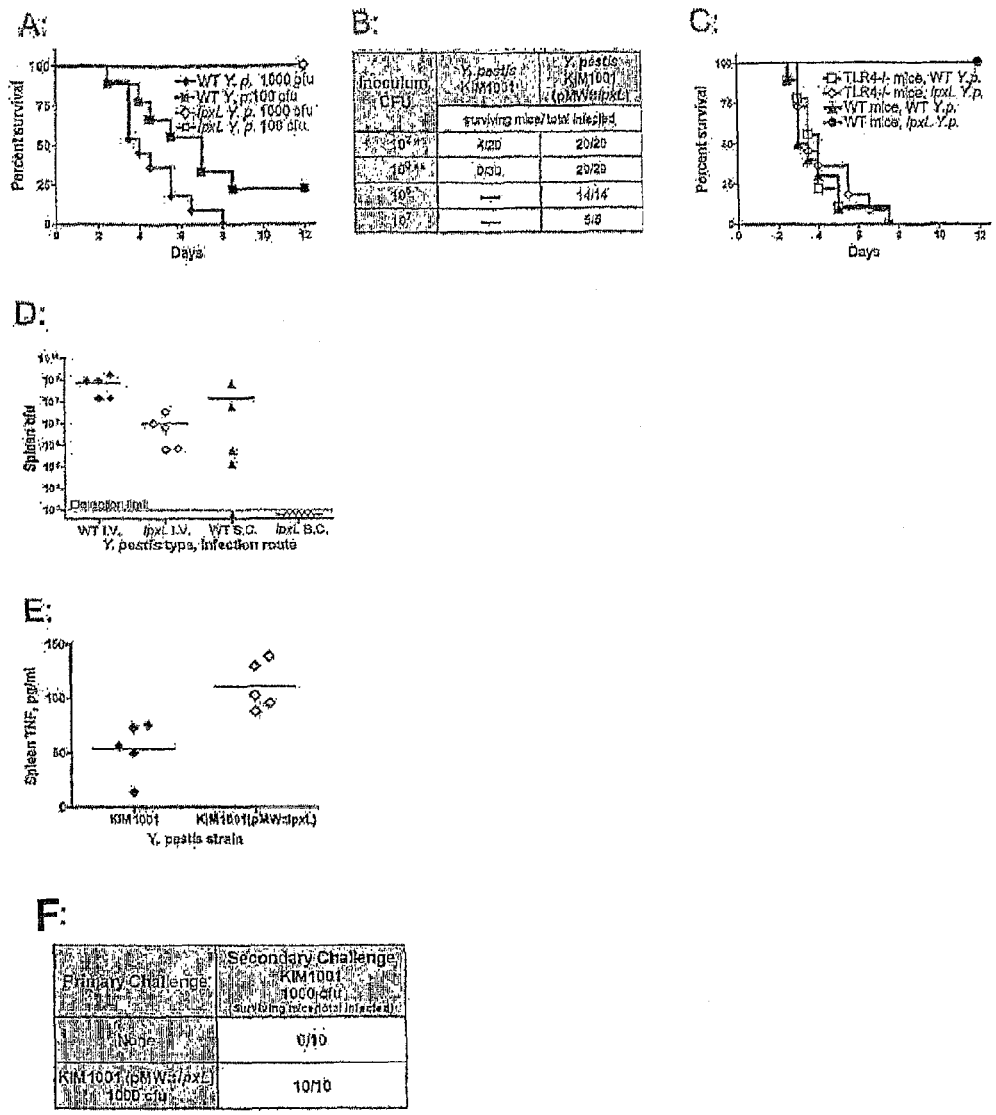

Mass spectroscopy (FIGS. 7C,D) shows that this strain contains hexa-acylated structures at both 37° C. and 26° C., indicating that, as in *E. coli, LpxL mediates addition of one* 2' secondary C12:0 acyl chain to lipid IV$_A$. Presumably, a 3' secondary C12:0 acyl moiety is added by the endogenous LpxM. In contrast to results obtained with KIM5 (FIG. 1, FIG. 3A), both 37° C. and 26° C. LPS from KIM5(pMW:: lpxL) strongly activated HEK293 huTLR4/MD2 cells (FIG. 3A), but not TLR2-expressing cells (FIG. 3B). A similar observation was made with human PBMC: only the KIM5

Figure 8:
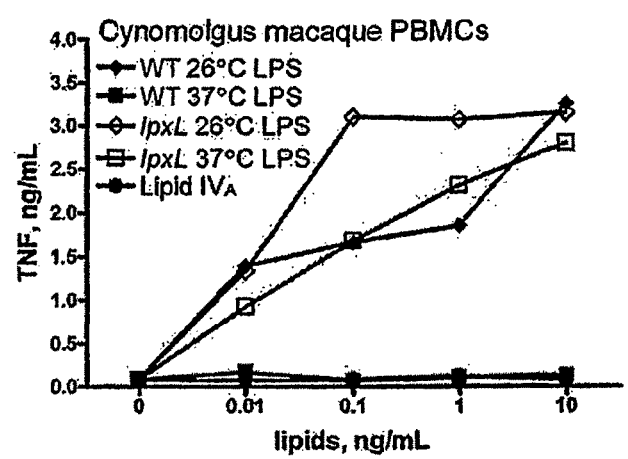

37° C. LPS showed profoundly reduced induction of TNF, IL-6, and IL-8 release (FIGS. 3C,D). Responses of human PBMC from several healthy volunteers (n=9) followed a similar pattern (not shown), as did PBMC from cynomolgus macaques (FIG. 8), indicating that primates have very low ability to respond to native 37° C. *Y. pestis* LPS. Mouse macrophages released limited amounts of TNF in a TLR4-dependent manner when exposed to the 37° C. LPS from KIM5, but this response was much weaker than observed with 37° C. LPS from KIM5(pMW::lpxL) or 26° C. LPS from either strain (FIGS. 3E,F). Thus, a major deficit in response to 37° C. *Y. pestis* LPS was common to cells from all species tested.

Mammals have multiple surveillance pathways that can trigger antibacterial responses. On the other hand, *Y. pestis* has sophisticated active mechanisms for suppressing these responses, including a type III secretion system that intoxicates host cells in contact with the bacteria (1, 2). To determine the significance of LPS stimulatory activity in this complex environment, we conducted infection experiments in mice. Virulent *Y. pestis* [strain KIM1001 (22)] induced 100% mortality in mice after subcutaneous (s.c.) injection of 1000 c.f.u. (FIG. 4A). In contrast, KIM1001(pMW::lpxL) caused neither mortality nor visible distress (FIG. 4A). The effect of LpxL is profound: at doses of up to $10^7$ c.f.u., approximately $10^6$ mean lethal doses for the KIM1001 parent strain, no mortality or apparent signs of illness were detected (FIG. 4B). Control experiments indicated that other *Y. pestis* virulence determinants were not affected by pMW::lpxL (Supporting text), and that pBR322 by itself had no effect on virulence (FIG. 9). Although the mouse TLR4/MD-2 system has a limited but significant response to tetra-acylated LPS/lipid A (FIG. 3E) (4, 23-25), it is apparently insufficient to protect infected mice. Our data suggest that the development of bubonic plague is dependent on the production of LPS with reduced TLR4/MD-2 stimulating activity.

This hypothesis predicts that resistance to KIM1001 (pMW::lpxL) should be TLR4-dependent. Accordingly, we infected both wild type and TLR4−/− mice with KIM1001 or KIM1001(pMW::lpxL) with a s.c. dose of 1000 c.f.u. Wild type and TLR4−/− animals succumbed to infection with KIM1001, while only TLR4−/− animals died when infected with KIM1001(pMW::lpxL) (FIG. 4C). In contrast, TLR4−/− animals survived infection with a *Y. pestis* Pla mutant, a strain that does not cause systemic infection by s.c. route (22), indicating that the TLR4−/− animals do not harbor a general defect in defense against other avirulent *Y. pestis* strains (Supporting text).

Foci of infection containing virulent *Y. pestis* are often devoid of inflammatory cells, reflecting the ability of this pathogen to evade immune responses. Intravenous (i.v.) infection is a useful model for examining inflammation in tissues remote from injection site trauma. When mice are infected i.v. with KIM1001(pMW::lpxL), enhanced anti-bacterial response is revealed by extended survival time (FIG. 10) and a 100-fold reduction (p=0.008) in spleen bacterial titers (FIG. 4D). Despite lower bacterial load, KIM1001(pMW::lpxL) infected animals had two-fold more TNF in spleen homogenates compared to mice infected with KIM1001 (FIG. 4E). Livers of mice infected with wild type *Y. pestis* are characterized by masses of free bacteria, without distinct indications of local inflammation. In contrast, KIM1001 (pMW::lpxL) provokes microabcess formation in livers from wild type mice, but not in TLR4−/− animals. Liver tissue was normal in animals receiving 1000 c.f.u. of KIM1001(pMW::lpxL) s.c.,, and no bacteria were detected in spleens (FIG. 4E). This indicates that s.c. administration of KIM1001 (pMW::lpxL) fails to establish systemic infection, presumably due to containment by effective local immunity.

We hypothesized that the avirulent *Y. pestis* (pMW::lpxL) producing potent LPS might be effective as a vaccine against plague. Mice were vaccinated with a single s.c. dose (1000 c.f.u.) of KIM1001(pMW::lpxL). Thirty-five days later, both vaccinated and naïve mice were challenged with virulent KIM1001 at an s.c. dose of 1000 c.f.u. All mice vaccinated with KIM1001(pMW::lpxL) survived while all naïve mice died (FIG. 4F), demonstrating that *Y. pestis* producing potent LPS is an effective vaccine.

In another experiment, mice were vaccinated s.c. with 100000 c.f.u. of KIM1001(pMW:::lpxL), and re-challenged with 100000 and 1000000 c.f.u. of KIM1001, days later. 5 out of 5 naïve mice die when infected with KIM1001, 100000 c.f.u., but 0 out of 5 mice died when they are vaccinated as given and re-challenged 30 days later with either 100000 or 1000000 c.f.u. of virulent KIM1001. These results indicate that the modified *Y. pestis* strain may be used as a vaccine against bubonic plague.

The following experiment shows that modified *Y. pestis* may also be used as a vaccine against pneumonic plague. Mice (wild type C57Bl/6) were vaccinated s.c. with 100000 c.f.u. of *Y. pestis* KIM1001(pMW:::lpxL) in the nape of the neck. 30 days later, the mice were challenged intranasally (i.n.) with 5000 or 50000 c.f.u. of virulent *Y. pestis KIM*1001. Intranasal challenge is a pneumonic plague model. Survival was monitored (five mice per vaccinated group, 8 mice in unvaccinated). The results, which are shown in FIG. 13, indicate that *Y. pestis* KIM1001(pMW:::lpxL) effectively protected mice against pneumonic plague.

Thus, these results indicate that generation of avirulent bacterial strains harboring enhanced TLR-activating potential could be a useful strategy for vaccine production.

The general picture that emerges from our current understanding of *Y. pestis* virulence is that successful systemic infection is dependent on efficient and simultaneous suppression and evasion of multiple pathways ordinarily capable of eliciting protective local inflammatory responses (1, 2, 22). Our results establish that evading activation of TLR4 signaling is an essential part of the *Y. pestis* strategy. These results also emphasize the remarkable efficiency of TLR4-mediated responses in the control of Gram-negative infections. Several other Gram-negative pathogens have been shown to synthesize lipid A with weak stimulatory activity, associated with differences in number and length of acyl chains (9, 10). To our knowledge, this is the first report to establish the significance of the synthesis of such lipid A for pathogenesis.

The strong TLR4-mediated protection against *Y. pestis* producing potent LPS suggests that the development of anti-infectives based on stimulation of innate immunity, now in its infancy, has significant promise (26, 27). However, incorporation of adjuvant activity into pathogens by LPS modification or other means may also be effectively applied as a novel principle for vaccines (28).

REFERENCES

1. R. D. Perry, J. D. Fetherston, *Clin Microbiol Rev* 10, 35-66 (1997).
2. G. R. Cornelis, *Nat Rev Mol Cell Biol* 3, 742-52 (2002).
3. K. Hoshino et al., *J Immunol* 162, 3749-52 (1999).
4. E. Lien et al., *J Clin Invest* 105, 497-504 (2000).
5. A. Poltorak et al., *Science* 282, 2085-2088 (1998).
6. C. R. Raetz, C. Whitfield, *Annu Rev Biochem* 71, 635-700 (2002).
7. S. Akira, K. Takeda, *Nat Rev Immunol* 4, 499-511 (2004).

8. R. Shimazu et al., *J Exp Med* 189, 1777-82 (1999).
9. U. Zahringer, B. Lindner, E. T. Rietschel, in *Endotoxin in Health and Disease* H. Brade, S. M. Opal, S. N. Vogel, D. C. Morrison, Eds. (Marcel Dekker, Inc., New York, 1999) pp. 93-114.
10. D. R. Dixon, R. P. Darveau, *J Dent Res* 84, 584-95 (2005).
11. K. Kawahara, H. Tsukano, H. Watanabe, B. Lindner, M. Matsuura, *Infect Immun* 70, 4092-8 (2002).
12. R. Rebeil, R. K. Ernst, B. B. Gowen, S. I. Miller, B. J. Hinnebusch, *Mol Microbiol* 52, 1363-73 (2004).
13. Y. A. Knirel et al., *Biochemistry* 44, 1731-43 (2005).
14. H. Loppnow et al., *J. Immunol.* 142, 3229-3238. (1989).
15. D. T. Golenbock, R. Y. Hampton, N. Qureshi, K. Takayama, C. R. H. Raetz, *J Biol Chem* 266, 19490-19498 (1991).
16. Materials and methods are available as supporting material on Science Online.
17. S. M. Carty, K. R. Sreekumar, C. R. Raetz, *J Biol Chem* 274, 9677-85 (1999).
18. M. K. Vorachek-Warren, S. M. Carty, S. Lin, R. J. Cotter, C. R. Raetz, *J Biol Chem* 277, 14186-93 (2002).
19. W. Deng et al., *J Bacteriol* 184, 4601-11 (2002).
20. R. D. Perry et al., *Infect Immun* 66, 4611-23 (1998).
21. J. Parkhill et al., *Nature* 413, 523-7 (2001).
22. O. A. Sodeinde et al., *Science* 258, 1004-7 (1992).
23. S. Akashi et al., *Int Immunol* 13, 1595-9 (2001).
24. A. M. Hajjar, R. K. Ernst, J. H. Tsai, C. B. Wilson, S. I. Miller, *Nat Immunol* 3, 354-9 (2002).
25. A. Poltorak, P. Ricciardi-Castagnoli, S. Citterio, B. Beutler, *Proc Natl Acad Sci USA* 97, 2163-7 (2000).
26. R. J. Ulevitch, *Nat Rev Immunol* 4, 512-20 (2004).
27. S. Agrawal, E. R. Kandimalla, *Ann N Y Acad Sci* 1002, 30-42 (2003).
28. Supplementary online information can be found on the Science web page.

Materials and Methods:
Bacterial Strains and Growth Conditions:
The lpxL gene from *E. coli* K12, including 435 bp upstream and 140 bp dowstream of coding region, was cloned using Pfu Ultra polymerase (Stratagene) and ligated into the BamHI and SalI sites of pBR322, creating pMW::lpxL. The control plasmid pBR322Δtet was constructed by digesting empty pBR322 with NaeI and EcoRV and then ligating the plasmid to remove the major part of the tetracycline resistant gene. The resulting plasmids were electroporated into *Yersinia pestis* strain KIM5 (Goguen et al., (1984) J Bacteriol 160, 842-8), or KIM1001 (Sodeinde et al., (1992) Science 258, 1004-7) and selected by growth on tryptose-beef extract (TB) agar supplemented with 2.5 mM $CaCl_2$ and 0.6 mg/mL glucose in the presence of 100 µg/ml ampicillin. All strains containing either pBR322Δtet or pMW::lpxL remained tetracycline sensitive. KIM1001 (pPCP1+, pCD1+, pMT1+) is highly virulent (Sodeinde et al., (1992) Science 258, 1004-7), while the KIM derivative KIM5 bears a chromosomal deletion designated Δpgm, which strongly attenuates virulence. KIM5 was used to limit risk of infection in in vitro studies where a virulent strain was not required, and the pgm locus contains no genes thought to impact LPS biosynthesis. For LPS or lipid A preparations, KIM5 and KIM5(pMW::lpxL) were grown overnight at the indicated temperatures in aerated TB broth supplemented with $CaCl_2$ and glucose as given above. For the generation of heat killed bacteria, cultures were resuspended in PBS and incubated at 60° C. for 1 hr.

Lipid Preparation:
Pyrogen-free reagents and supplies were used to the greatest extent possible in the lipid preparations. Bacteria were harvested by centrifugation at 6000×g. Lipid A was directly isolated from whole bacterial cells using the Bligh-Dyer two-phase chloroform-methanol-water organic extraction (Vorachek-Warren et al., (2002) J Biol Chem 277, 14186-93). Samples were subsequently analyzed by MALDI-TOF MS using a Kratos (Manchester, UK) AXIMA CFR high performance mass spectrometer operated in both positive and negative ion modes. LPS was purified from bacteria by hot water-phenol extraction (Westphal et al., (1952) Naturforsch. B7, 148-155), followed by two phenol re-extractions to remove contaminating lipoproteins and TLR2-activity (Hirschfeld et al., (2000) J Immunol 165, 618-622). The chemical synthesis of the tetra-acylated precursor lipid WA (also called 406, LA-14-PP or precursor Ia) has been reported (Liu et al., (1999) Bull. Chem. Soc. Jpn. 72, 1377-1385). LPS from *E. coli* O111:B4 (Sigma) was phenol re-extracted as indicated above. The LPS preparations were unable to stimulate HEK293 huTLR2-expressing cells, in spite of strong cellular activation by Pam3CysSK4 lipopeptide, indicating the absence of contaminating lipoproteins in our LPS (FIG. 3B and not shown).

Cell Stimulation Assays:
Human PBMC were obtained from healthy volunteers and isolated by centrifugation on Lympoprep density media (Axis-Shield/Nycomed, Oslo, Norway). Cynomolgous macaque PBMC, purified by centrifugation of whole blood in CPT/sodium citrate tubes (Becton Dickinson), was obtained from Bioreclamation, Inc (Hicksville, N.Y.). HEK293 cells stably expressing human TLR4-YFP and retroviral MD-2, or human TLR2-YFP, or empty vector pcDNA3 were as published (Latz et al., (2002) J Biol Chem 277, 47834-43). No activation of the HEK293 huTLR2-expressing cell line was observed by our LPS preparations, in spite of strong activation by Pam3CysSK4 lipopeptide, suggesting absence of contaminating lipoprotein in the LPS. NF-κB-luciferase (provided by K. Fitzgerald) and IRF-3-dependent 561-luciferase [a gift from G. Sen (Bandyopadhyay et al., (1995) J Biol Chem 270, 19624-9)] reporters were transfected into 293-huTLR4/MD-2 cells using Genejuice (Novagen). PBMC were cultured in X-vivo 15 medium (Cambrex) containing ciprofloxacin and 1% FCS or 1% human serum, whereas 293 cells were stimulated in DMEM/ciprofloxacin plus 10% FCS. Wild type C57Bl/6 mice were from Jackson Laboratories (Bar Harbor, Me.). TLR4-/- animals, a gift from Dr. S. Akira, were generated as described (Hoshino et al., (1999) J Immunol 162, 3749-52), and backbred 11 generations into C57Bl/6. Mouse peritoneal macrophages were harvested from wild type C57Bl/6 or TLR4-/- mice 3 days after injection of 2 ml thioglycollate (3%) and cultured in RPMI 1640 medium containing 10% FCS. Cells were plated at a density of $2 \times 10^4$ cells/well (293 cells) $5 \times 10^4$ cells/well (mouse macrophages) or $1 \times 10^5$ cells/well (PBMC) in 96-well dishes, and stimulated 16-18 hrs before harvesting supernatant (for cytokine analysis) or cells for lysis (transfections and reporter assays, using reagents from Promega). Cytokines were measured using ELISA kits from BD Pharmingen (moTNFα) or R&D systems (huTNFα, IL-6, IL-8). Cell lysates from luciferase reporter assays were analyzed by the addition of luciferase substrate followed by luminometry. Results are shown as one representative out of three to eight experiments, as mean of triplicates (transfection assays) or triplicates/duplicates (cytokine assays)+/- standard deviation (s.d.).

In Vivo Infections:
Mice were infected with *Y. pestis* KIM1001, KIM1001 (pMW::lpxL) or KIM1001(pBR322Δtet), either by s.c. injection of 50 µl on the nape of the neck or i.v. injection of 500 µl in the tail vein. Inocula contained the indicated c.f.u. suspended in PBS. Survival was monitored up to 21 days, every 12 hrs during acute infection. For collection of organs, mice were sacrificed 48 hrs following i.v. infection or 72 hrs following s.c. infection by pentobarbital overdose, spleens were homogenized in PBS for bacterial titers. Separate infection experiments with detection limits of $10^3$ or $10^1$ c.f.u. per spleen showed similar results, with the absence of detectable bacteria in spleens following s.c. infection with KIM1001 (pMW::lpxL). Livers were fixed for 3 days in neutral buffered 4% formalin, followed by standard hematoxylin/eosin (H&E) staining and microscopy (100× magnification). Inserts [KIM1001 and KIM1001(pMW::lpxL) i.v.] are at 1000× magnification. All animal studies were approved by the Institutional Animal Care and Use Committee. Differences in spleen c.f.u and TNF concentrations were analyzed by Mann-Whitney U-test. Statistical differences in survival were studied by Kaplan-Meyer survival analysis and the log rank test.

Supporting Text:

*Y. pestis* Grown at 37° Poorly Activates TLR4 Signaling

Figure 9:
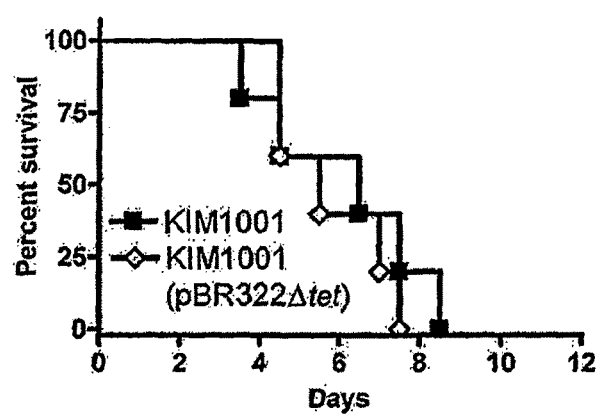
Figure 10:
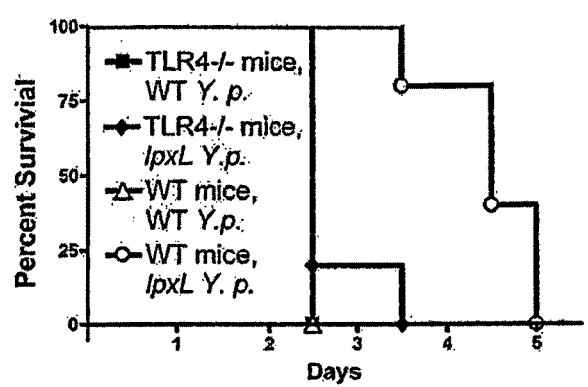

When grown at 26° C., heat-killed *Y. pestis* KIM5, an attenuated strain deficient in iron acquisition, strongly activates HEK293 huTLR4/MD-2 cells to release IL-8 and to activate transcription factors NF-κB and IRF-3 (FIGS. 9*a, b*). If the bacteria are grown at 37° C., this activation is not observed. Activation and nuclear translocation of these two transcription factors constitute two major branches of TLR4 signaling necessary for the induction of pro-inflammatory cytokines and type I interferons (Akira et al., (2004) Nat Rev Immunol 4, 499-511; Liew et al., (2005) Nat Rev Immunol 5, 446-58). These data, together with the presence of poorly immune activating tetra-acylated *Y. pestis* lipid A structures at 37° C. (Kawahara et al., (2002) Infect Immun 70, 4092-8; Rebeil et al., (2004) Mol Microbiol 52, 1363-73), suggest that evasion of TLR4-signaling could represent a central mechanism by which *Y. pestis* avoids innate immune activation.

*Y. pestis* Containing (pMW::lpxL) Retains Key Features

To further ensure that important virulence-related functions of *Y. pestis* that might be altered by changes in membrane structure were not affected by lpxL, we confirmed that pMW::lpxL did not affect the function of type III secretion activity as evidenced by secretion of YopM, retention of cytotoxic activity for HeLa cells in vitro, and retention of $Ca^{++}$-dependent growth at 37° C., and also did not affect the ability of the outer membrane protease Pla to act on the high molecular weight substrate plasminogen. We also determined that pMW::lpxL was stable in the absence of selection (no plasmids segregants detected among 1000 colonies after 40 generations of growth in liquid culture), and that native Y perils plasmids were retained in the presence of pMW::lpxL.

Bacteria obtained from spleens of mice infected i.v. with KIM1001(pMW::lpxL) all remained ampicillin resistant following patching of 100 colonies. Furthermore, the presence of the control plasmid pBR322Δtet in KIM1001 did not affect virulence in mice (FIG. 9).

TLR4−/− Mice Survive Infection with Pla Mutant *Y. pestis*

*Y. pestis* KIM1001(pMW::lpxL) is avirulent in wt mice, but fully virulent in TLR4−/− animals. We also considered the possibility that TLR4 deficiency would alter the susceptibility to other types of *Y. pestis* strains that are avirulent by s.c. infection. To test this, we infected mice with *Y. pestis* KIM lacking the outer membrane protease known as plasminogen activator (Pla) (Sodeinde et al., (1992) Science 258, 1004-7). Pla clearly contributes to suppressing local inflammation, although the mechanism of this contribution is currently not known. We have previously shown that this strain, like KIM expressing lpxL, is avirulent by s.c. infection but virulent when given i.v., and provokes substantial local inflammation (Sodeinde et al., (1992) Science 258, 1004-7). Thus, survival of infection with this strain also depends on vigorous local innate responses. If the effect of TLR4 on innate responses is non-specific, TLR4-deficient mice should be susceptible to $Pla^-$ *Y. pestis*. All of three TLR4−/− mice infected with the $Pla^-$ strain (Sodeinde et al., (1992) Science 258, 1004-7) s.c. at $10^5$ c.f.u. survived, showed no signs of illness, and were immune to later challenge with wild type KIM confirming infection. This result indicates that TLR4 deficiency does not grossly compromise innate responses to *Y. pestis* in general, and that loss of Pla and production of stimulatory LPS, while both permitting effective innate responses, do so via distinct pathways.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. A transgenic gram-negative bacterium that is derived from a wild-type bacterium that does not comprise high potency lipopolysaccharide (LPS), wherein said transgenic bacterium makes said high potency lipopolysaccharide (LPS), and comprises a heterologous nucleic acid sequence encoding an acyltransferase that permits the transgenic bacterium to produce high potency LPS,
   a) wherein the heterologous nucleic acid sequence is at least about 80% identical to a nucleic acid sequence comprising SEQ ID NO: 1,
   b) wherein said nucleic acid sequence encodes a LPS biosynthetic enzyme LpxL or a LpxL functional analog,
   c) wherein said LpxL or said LpxL functional analog comprises an amino acid sequence which is at least about 90% identical to SEQ ID NO: 4, and
   d) wherein said transgenic bacterium has reduced virulence relative to a control bacterium that contains a mutation in said heterologous nucleic acid sequence.

2. The gram-negative bacterium of claim 1, wherein the high potency LPS activates Toll-like receptor 4 (TLR4) in mammalian cells.

3. The gram negative bacterium of claim 2, wherein the high potency LPS is hexa-acylated LPS.

4. The grain negative bacterium of claim 3, wherein the bacterium is selected from the group consisting of Yersinia pestis, Chlamydia trachomatis, Francisella tularensis, Legionella pneumophila, Brucella abortus and Chlamydia pneumoniae.

5. The gram negative bacterium of claim 4, which is Yersinia pestis.

6. The gram negative bacterium of claim 5, wherein the enzyme LpxL is from E. coli and comprises SEQ ID NO: 4.

7. The gram negative bacterium of claim 1, which is alive.

8. The gram negative bacterium of claim 1, which is killed.

9. A composition comprising at least about 100 colony forming units (c.f.u.) of the gram-negative bacterium of claim 1.

10. A composition comprising at least about 1,000 c.f.u. of the gram-negative bacterium of claim 1.

11. A vaccine comprising the composition of claim 9 or 10 further comprising a pharmaceutically acceptable carrier.

12. The gram negative bacterium of claim 1, wherein said heterologous nucleic acid sequence comprises a nucleotide sequence which is at least about 85%, 90%, 92%, 94%, 95%, 96%, 97%, 98%, or 99% identical to a nucleic acid sequence comprising the nucleotide sequence of SEQ ID NO: 1.

13. A transgenic gram-negative bacterium that is derived from a wild-type bacterium that does not comprise high potency lipopolysaccharide (LPS), wherein said transgenic bacterium comprises a heterologous nucleic acid sequence encoding an acyltransferase,
   a) wherein the heterologous nucleic acid sequence is at least about 80% identical to a nucleic acid sequence comprising SEQ ID NO: 1,
   b) wherein said nucleic acid sequence encodes a LPS biosynthetic enzyme LpxL or a LpxL functional analog,
   c) wherein said LPS biosynthetic enzyme LpxL or a LpxL functional analog comprises an amino acid sequence which is at least about 90%, 92%, 94%, 95%, 96%, 97%, 98%, or 99% identical to the amino acid sequence comprising the amino acid sequence of SEQ ID NO: 4, and
   d) wherein said transgenic bacterium has reduced virulence relative to a control bacterium that contains a mutation in said heterologous nucleic acid sequence.

14. The gram-negative bacterium of claim 1, wherein said transgenic bacterium has at least 10-fold reduced virulence relative to said control bacterium.

15. The gram-negative bacterium of claim 14, wherein said transgenic bacterium is Yersinia pestis and is avirulent in wild type mouse.

16. A method for protecting a mammal from infection by a gram-negative pathogen, comprising administering to a mammal in need thereof an effective amount of a composition comprising the gram-negative bacterium of claim 1.

17. The method of claim 16, wherein said gram-negative bacterium is Yersinia pestis.

18. A method for delivering an antigen to a subject, comprising delivering to a subject in need thereof a therapeutically effective amount of the gram-negative bacterium of claim 1, wherein said gram-negative bacterium further comprises an antigen.

19. The gram-negative bacterium of claim 1, wherein said heterologous nucleic acid sequence is SEQ ID NO: 1, and said LpxL is SEQ ID NO: 4.

20. A transgenic gram-negative bacterium that is derived from a wild-type bacterium that does not comprise high potency lipopolysaccharide (LPS), wherein said transgenic bacterium makes said high potency lipopolysaccharide (LPS), and comprises a heterologous nucleic acid sequence encoding an acyltransferase that permits the transgenic bacterium to produce high potency LPS,
   a) wherein said heterologous nucleic acid sequence is at least about 80% identical to a nucleic acid sequence comprising SEQ ID NO: 1,
   b) wherein said nucleic acid sequence encodes a LPS biosynthetic enzyme LpxL or a LpxL functional analog,
   c) wherein said LpxL or said LpxL functional analog comprises an amino acid sequence which is at least about 90% identical to SEQ ID NO: 4,
   d) wherein said transgenic bacterium has reduced virulence relative to a control bacterium that contains a mutation in said heterologous nucleic acid sequence, and e) wherein said wild-type bacterium is selected from the group consisting of *Yersinia pestis, Chlamydia trachomatis, Francisella tularensis, Legionella pneumophila, Brucella abortus* and *Chlamydia pneumoniae.*

* * * * *